United States Patent
Chuang et al.

(10) Patent No.: US 9,793,673 B2
(45) Date of Patent: Oct. 17, 2017

(54) SEMICONDUCTOR INSPECTION AND METROLOGY SYSTEM USING LASER PULSE MULTIPLIER

(75) Inventors: Yung-Ho Chuang, Cupertino, CA (US); J. Joseph Armstrong, Fremont, CA (US); Justin Dianhuan Liou, Santa Clara, CA (US); Vladimir Dribinski, Livermore, CA (US); David L. Brown, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 667 days.

(21) Appl. No.: 13/487,075

(22) Filed: Jun. 1, 2012

(65) Prior Publication Data
US 2012/0314286 A1 Dec. 13, 2012

Related U.S. Application Data

(60) Provisional application No. 61/496,446, filed on Jun. 13, 2011.

(51) Int. Cl.
*G02B 5/30* (2006.01)
*G02B 27/28* (2006.01)
(Continued)

(52) U.S. Cl.
CPC ........... *H01S 3/0057* (2013.01); *G01N 21/21* (2013.01); *G01N 21/9501* (2013.01);
(Continued)

(58) Field of Classification Search
CPC .. G02B 5/3083; G02B 27/283; G02B 27/286; H01S 3/0057; H01S 3/083
(Continued)

(56) References Cited

U.S. PATENT DOCUMENTS

| 4,644,221 A | 2/1987 | Gutierrez et al. |
| 4,710,030 A | 12/1987 | Tauc et al. |

(Continued)

FOREIGN PATENT DOCUMENTS

| JP | H0511287 A | 1/1993 |
| JP | H08241977 A | 9/1996 |

(Continued)

OTHER PUBLICATIONS

International Search Report and Written Opinion dated Mar. 19, 2014 for PCT/US2013/072774 filed Dec. 3, 2013 in the name of KLA-Tencor Corporation (14 pages).

(Continued)

*Primary Examiner* — Ricky D Shafer
(74) *Attorney, Agent, or Firm* — Bever, Hoffman & Harms, LLP

(57) ABSTRACT

A pulse multiplier includes a polarizing beam splitter, a wave plate, and a set of mirrors. The polarizing beam splitter receives an input laser pulse. The wave plate receives light from the polarized beam splitter and generates a first set of pulses and a second set of pulses. The first set of pulses has a different polarization than the second set of pulses. The polarizing beam splitter, the wave plate, and the set of mirrors create a ring cavity. The polarizing beam splitter transmits the first set of pulses as an output of the pulse multiplier and reflects the second set of pulses into the ring cavity. This pulse multiplier can inexpensively reduce the peak power per pulse while increasing the number of pulses per second with minimal total power loss.

12 Claims, 19 Drawing Sheets

(51) Int. Cl.
*H01S 3/05* (2006.01)
*H01S 3/083* (2006.01)
*H01S 3/00* (2006.01)
*G01N 21/21* (2006.01)
*G01N 21/95* (2006.01)
*G02B 5/08* (2006.01)

(52) U.S. Cl.
CPC ......... *G02B 5/0816* (2013.01); *G02B 5/3083* (2013.01); *G02B 27/281* (2013.01); *G02B 27/283* (2013.01); *G02B 27/286* (2013.01); *H01S 3/083* (2013.01); *G01N 2201/0683* (2013.01); *G01N 2201/0697* (2013.01); *G01N 2201/06113* (2013.01)

(58) Field of Classification Search
USPC .................. 359/489.07, 489.08, 900, 489.15; 372/30, 94, 105, 99, 106
See application file for complete search history.

(56) References Cited

U.S. PATENT DOCUMENTS

| | | | |
|---|---|---|---|
| 4,718,766 A * | 1/1988 | Greenstein | 356/472 |
| 4,853,595 A | 8/1989 | Alfano et al. | |
| 4,999,014 A | 3/1991 | Gold et al. | |
| 5,119,382 A * | 6/1992 | Kennedy et al. | 372/11 |
| 5,144,630 A | 9/1992 | Lin | |
| 5,172,382 A * | 12/1992 | Loh et al. | 372/26 |
| 5,189,481 A | 2/1993 | Jann et al. | |
| 5,276,548 A * | 1/1994 | Margalith | 359/330 |
| 5,309,456 A | 5/1994 | Horton | |
| 5,563,702 A | 10/1996 | Emery et al. | |
| 5,742,626 A | 4/1998 | Mead et al. | |
| 5,760,809 A | 6/1998 | Malhotra et al. | |
| 5,760,899 A | 6/1998 | Eismann | |
| 5,999,310 A | 12/1999 | Shafer et al. | |
| 6,064,759 A | 5/2000 | Buckley et al. | |
| 6,201,601 B1 | 3/2001 | Vaez-Iravani et al. | |
| 6,233,052 B1 * | 5/2001 | Zare et al. | 356/437 |
| 6,271,916 B1 | 8/2001 | Marxer et al. | |
| 6,275,514 B1 | 8/2001 | Katzir | |
| 6,373,869 B1 | 4/2002 | Jacob | |
| 6,535,531 B1 | 3/2003 | Smith et al. | |
| 6,549,267 B1 * | 4/2003 | Kudo | 355/53 |
| 6,577,782 B1 | 6/2003 | Leaird et al. | |
| 6,608,676 B1 | 8/2003 | Zhao et al. | |
| 6,693,930 B1 | 2/2004 | Chuang et al. | |
| 6,734,968 B1 | 5/2004 | Wang et al. | |
| 6,816,520 B1 * | 11/2004 | Tulloch et al. | 372/22 |
| 7,151,632 B2 * | 12/2006 | Biss et al. | 359/371 |
| 7,187,500 B2 | 3/2007 | Chuang et al. | |
| 7,313,155 B1 | 12/2007 | Mu | |
| 7,321,468 B2 | 1/2008 | Herkommer et al. | |
| 7,352,457 B2 | 4/2008 | Kvamme et al. | |
| 7,449,673 B2 | 11/2008 | Chuang et al. | |
| 7,525,649 B1 | 4/2009 | Leong et al. | |
| 7,528,342 B2 | 5/2009 | Deshi | |
| 7,528,943 B2 | 5/2009 | Brown et al. | |
| 7,609,309 B2 | 10/2009 | Brown et al. | |
| 7,667,841 B2 | 2/2010 | Opsal | |
| 7,813,406 B1 | 10/2010 | Nguyen et al. | |
| 7,952,633 B2 | 5/2011 | Brown et al. | |
| 7,999,342 B2 | 8/2011 | Hsu et al. | |
| 8,309,443 B2 | 11/2012 | Tanaka et al. | |
| 8,514,587 B2 | 8/2013 | Zhang et al. | |
| 8,624,971 B2 | 1/2014 | Brown et al. | |
| 8,686,331 B2 | 4/2014 | Armstrong | |
| 8,748,828 B2 | 6/2014 | Brown et al. | |
| 8,754,972 B2 | 6/2014 | Brown et al. | |
| 8,755,417 B1 | 6/2014 | Dribinski | |
| 8,873,596 B2 * | 10/2014 | Dribinski et al. | 372/18 |
| 8,929,406 B2 * | 1/2015 | Chuang et al. | 372/5 |
| 2002/0191834 A1 | 12/2002 | Fishbaine | |
| 2003/0043876 A1 | 3/2003 | Lublin et al. | |
| 2004/0095573 A1 | 5/2004 | Tsai et al. | |
| 2005/0110988 A1 * | 5/2005 | Nishiyama et al. | 356/237.5 |
| 2005/0122021 A1 | 6/2005 | Smith et al. | |
| 2005/0190452 A1 | 9/2005 | Govorkov et al. | |
| 2006/0126681 A1 | 6/2006 | Botma et al. | |
| 2006/0126682 A1 | 6/2006 | Rodin et al. | |
| 2006/0171036 A1 | 8/2006 | Govorkov et al. | |
| 2007/0002465 A1 | 1/2007 | Chuang et al. | |
| 2007/0047600 A1 | 3/2007 | Luo et al. | |
| 2007/0090278 A1 | 4/2007 | Botma | |
| 2007/0096648 A1 | 5/2007 | Nakajima et al. | |
| 2007/0103769 A1 | 5/2007 | Kuwabara | |
| 2007/0121107 A1 | 5/2007 | Tsai et al. | |
| 2007/0188744 A1 | 8/2007 | Leslie et al. | |
| 2007/0291810 A1 | 12/2007 | Luo et al. | |
| 2007/0295974 A1 | 12/2007 | Fontanella | |
| 2008/0173903 A1 | 7/2008 | Imai et al. | |
| 2008/0182092 A1 | 7/2008 | Bondokov et al. | |
| 2008/0267241 A1 | 10/2008 | Brown et al. | |
| 2009/0052480 A1 | 2/2009 | Cobb et al. | |
| 2009/0080085 A1 | 3/2009 | Botma | |
| 2009/0108207 A1 | 4/2009 | Liu | |
| 2009/0128912 A1 | 5/2009 | Okada | |
| 2009/0180176 A1 | 7/2009 | Armstrong et al. | |
| 2010/0103409 A1 | 4/2010 | Ohshima et al. | |
| 2010/0108913 A1 | 5/2010 | Ershov et al. | |
| 2010/0163757 A1 | 7/2010 | Joobeur et al. | |
| 2010/0301437 A1 | 12/2010 | Brown | |
| 2011/0073982 A1 | 3/2011 | Armstrong et al. | |
| 2011/0228263 A1 | 9/2011 | Chuang et al. | |
| 2011/0279819 A1 | 11/2011 | Chuang et al. | |
| 2012/0026578 A1 | 2/2012 | Sakuma | |
| 2013/0009069 A1 | 1/2013 | Okada | |
| 2013/0016346 A1 | 1/2013 | Romanovsky et al. | |
| 2013/0020491 A1 | 1/2013 | Mazzillo | |
| 2013/0077086 A1 * | 3/2013 | Chuang et al. | 356/51 |
| 2013/0088706 A1 | 4/2013 | Chuang et al. | |
| 2013/0126705 A1 | 5/2013 | Maleev | |
| 2013/0169957 A1 | 7/2013 | Wolf et al. | |
| 2013/0264481 A1 | 10/2013 | Chern et al. | |
| 2013/0313440 A1 | 11/2013 | Chuang et al. | |
| 2013/0336574 A1 | 12/2013 | Nasser-Ghodsi et al. | |
| 2014/0016655 A1 | 1/2014 | Armstrong | |
| 2014/0050234 A1 | 2/2014 | Ter-Mikirtychev | |
| 2014/0111799 A1 | 4/2014 | Lei et al. | |
| 2014/0153596 A1 | 6/2014 | Chuang et al. | |
| 2014/0158864 A1 | 6/2014 | Brown et al. | |
| 2014/0226140 A1 | 8/2014 | Chuang et al. | |
| 2014/0291493 A1 | 10/2014 | Chuang et al. | |
| 2014/0305367 A1 | 10/2014 | Chuang et al. | |
| 2015/0007765 A1 | 1/2015 | Dribinski | |
| 2015/0177159 A1 | 6/2015 | Brown et al. | |
| 2015/0200216 A1 | 7/2015 | Muramatsu et al. | |
| 2015/0275393 A1 | 10/2015 | Bondokov et al. | |
| 2015/0294998 A1 | 10/2015 | Nihtianov | |

FOREIGN PATENT DOCUMENTS

| | | |
|---|---|---|
| JP | 2002033473 | 1/2002 |
| JP | 2003043533 A | 2/2003 |
| JP | 2005148550 A | 6/2005 |
| JP | 2006-186046 A | 7/2006 |
| JP | 200786108 | 4/2007 |
| JP | 2007085958 A | 4/2007 |
| JP | 2007511908 A | 5/2007 |
| JP | 2007249092 A | 9/2007 |
| JP | 2007298932 A | 11/2007 |
| JP | 2009076906 A | 4/2009 |
| JP | 2010003755 | 1/2010 |
| JP | 2012-098103 A | 5/2012 |
| KR | 10-2000-0034461 A | 6/2000 |
| KR | 1020100025297 A | 3/2010 |
| WO | 00/14834 A1 | 3/2000 |
| WO | WO2010/037106 A2 | 4/2010 |
| WO | 2010037106 A3 | 6/2010 |
| WO | 2011041472 A1 | 4/2011 |
| WO | 2011/064059 A1 | 6/2011 |

(56) References Cited

FOREIGN PATENT DOCUMENTS

| WO | 2012091786 A1 | 7/2012 |
|---|---|---|
| WO | 2014067754 A2 | 5/2014 |

OTHER PUBLICATIONS

Herriott et al.: "Off-Axis Paths in Spherical Mirror Interferometers", Applied Optics 3, #4, pp. 523-526 (1964).
Herriott et al.: "Folded Optical Delay Lines", Applied Optics 4, #6, pp. 883-889 (1965).
White, John U.: "Long Optical Paths of Large Aperture", Journal of the Optical Society of America 32. #5, pp. 285-288 (1942).
KLA-Tencor Corporation; PCT International Search Report dated Dec. 29, 2015 for Application No. PCT/US2015/051538, 3 pages.
KLA-Tencor Corporation, U.S. Appl. No. 14/248,045, filed Apr. 8, 2014 and entitled "Passivation of Nonlinear Optical Crystals".
KLA-Tencor Corporation, U.S. Appl. No. 62/059,368, filed Oct. 3, 2014 and entitled "183nm Laser and Inspection System".
KLA-Tencor Corpoation, U.S. Appl. No. 14/210,355, filed Mar. 13, 2014 and entitled "193nm Laser and an Inspection System Using a 193nm Lasser".
Raoult, F. et al., "Efficient generation of narrow-bandwidth picosecond pulses by frequency doubling of femtosecond chirped pulses", Jul. 15, 1998 / ol. 23, No. 14 / Optics Letters, pp. 1117-1119.
Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.
Itzler, Mark et al., "InP-based Geiger-mode avalanche photodiode arrays for three-dimensional imaging at 1.06 μm", Proceedings of SPIE, vol. 7320 (2000), 12 pages.
Niclass, Cristiano et al., "Design and Characterization of a CMOS 3-D Image Sensor Based on Single Photon Avalanche Diodes", IEEE Journal of Solid-State Circuits, vol. 40, No. 9, Sep. 2005, 8 pages.
Paetzel, Rainer et al., "Activation of Silicon Wafer by Excimer Laser" 18th IEEE Conf. Advanced Thermal processing of Semiconductors—RTP 2010, 5 pages.
Stevanovic, Nenad et al., "A CMOS Image Sensor for High-Speed Imaging", 2000 IEEE Int'l. Conference Solid-State Circuits, 3 pages.
Dulinski, Wojciech et al., "Tests of a backside illuminated monolithic CMOS pixel sensor in an HPD set-up", Nuclear Instruments and Methods in Physics Research a 546 (2005) 274-280, 7 pages.
Sarubbi, F et al, "Pure boron-doped photodiodes: a solution for radiation detection in EUV lithography", Proceedings of the 38th EP Solid-State Device Research Conf., Edinburgh Int'l. Conf. Centre, Endiburgh, Scotland, UK, Sep. 15-19, 2008, Piscataway, NJ: IEEE, US, pp. 278-281.
Sakic, Agata, "Boron-layer silicon photodiodes for high-efficiency low-energy electron detection", Solid-State Electronics 65-66 (2011), pp. 38-44.
Omatsu, Takashige et al., "High repetition rate Q-switching performance in transversely diode-pumped Nd doped mixed gadolinium yttrium vanadate bounce laser", Optics Express vol. 14, Issue 7, pp. 2727-2734, Apr. 3, 2006.

\* cited by examiner

FIG. 3A
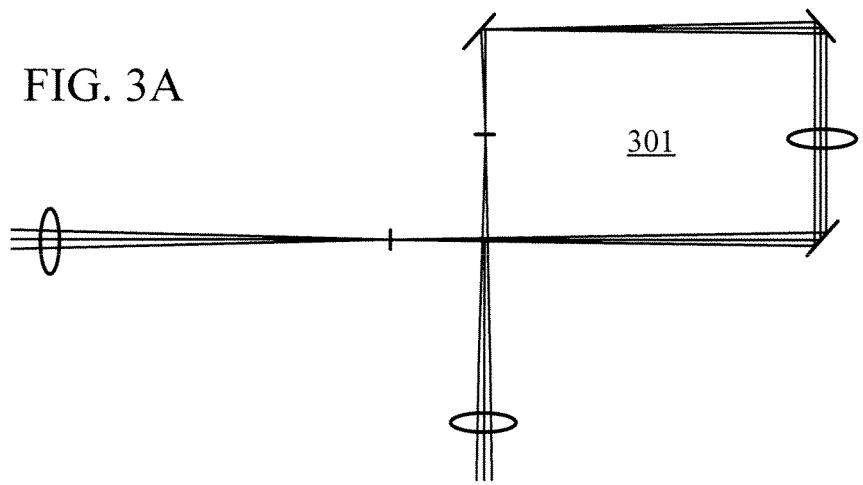
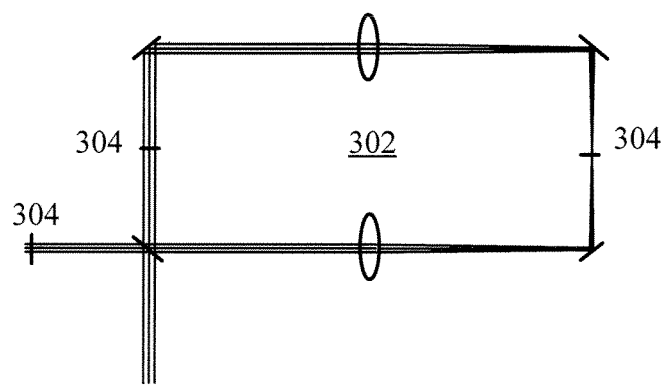
FIG. 3B
FIG. 3C
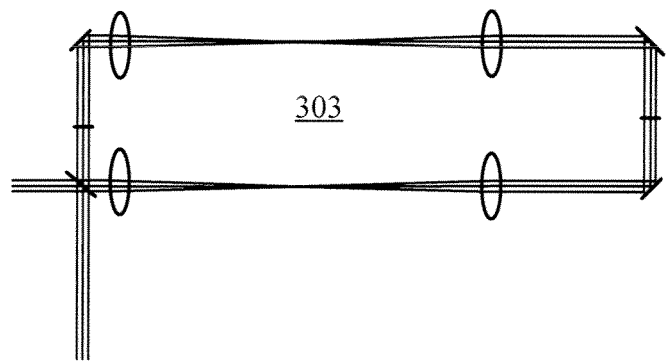

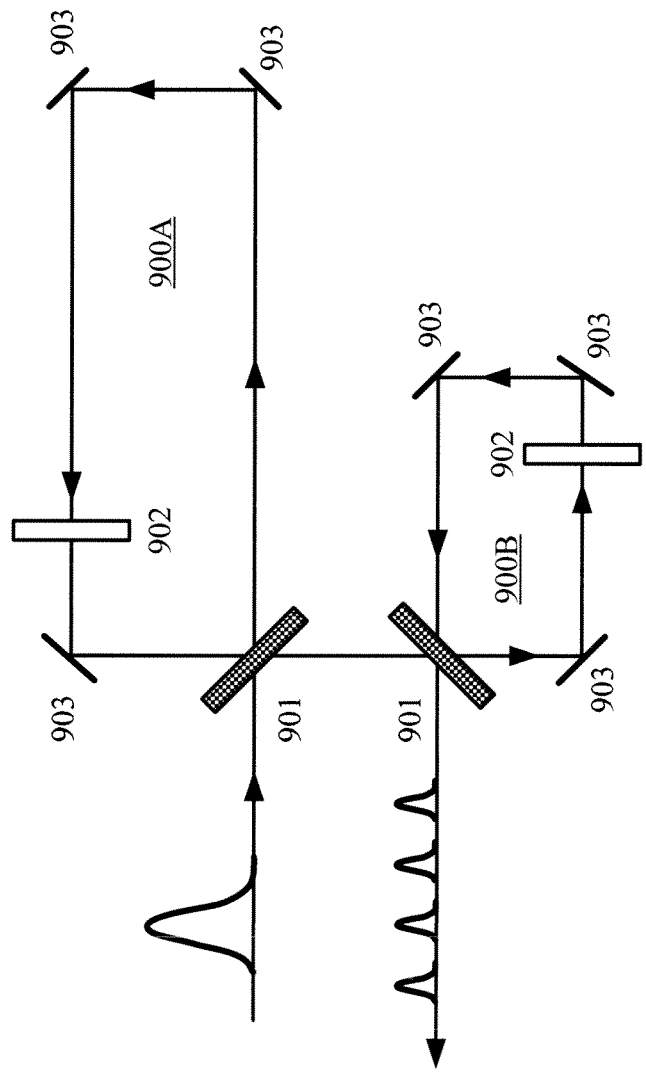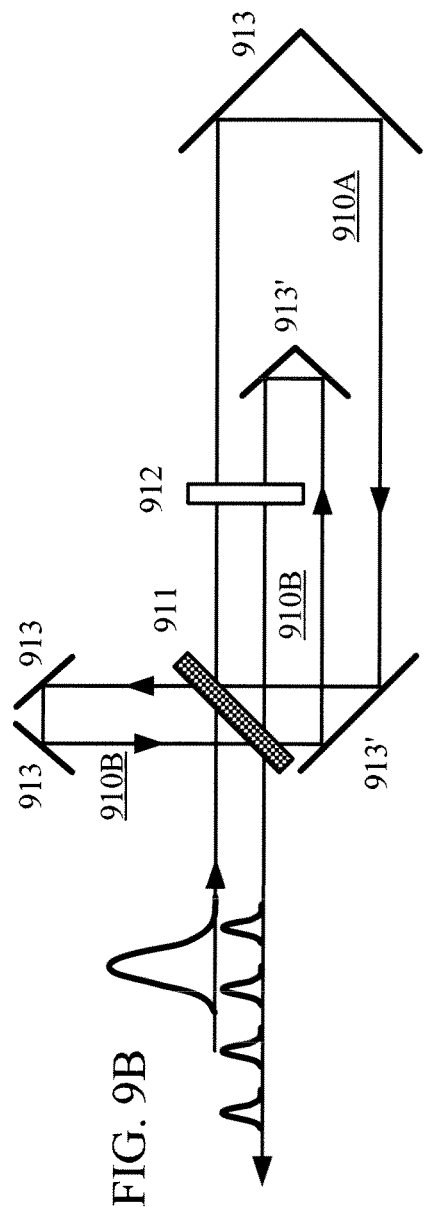
FIG. 9A
FIG. 9B

SEMICONDUCTOR INSPECTION AND METROLOGY SYSTEM USING LASER PULSE MULTIPLIER

RELATED APPLICATIONS

This application claims priority of U.S. Provisional Patent Application 61/496,446, entitled "Optical Peak Power Reduction Of Laser Pulses And Semiconductor Inspection And Metrology Systems Using Same" filed Jun. 13, 2011.

BACKGROUND OF THE INVENTION

1. Field of the Invention

The present invention relates to using optical peak power reduction of laser pulses for semiconductor inspection and metrology systems, and in particular to using a polarizing beam splitter and a wave plate to generate an optimized pulse multiplier.

2. Related Art

The illumination needs for inspection and metrology are generally best met by continuous wave (CW) light sources. A CW light source has a constant power level, which allows for images or data to be acquired continuously. However, at many wavelengths of interest, particularly UV wavelengths, CW light sources of sufficient radiance (power per unit area per unit solid angle) are not available.

A pulsed light source has an instantaneous peak power level much higher than the time-averaged power level of a CW light source. However, if a pulsed laser is the only available, or cost-effective, light source with sufficient time-averaged radiance at the wavelength of interest, then using a laser with the highest possible repetition rate and greatest pulse width is optimal. The higher the pulse repetition rate, the lower the instantaneous peak power per pulse for the same time-averaged power level. The lower peak power of the laser pulses results in less damage to the optics and to the wafer being measured, as most damage mechanisms are non-linear and depend more strongly on peak power rather than on average power.

An additional advantage of an increased repetition rate is that more pulses are collected per data acquisition or per pixel leading to better averaging of the pulse-to-pulse variations and better signal-to-noise ratios. Furthermore, for a rapidly moving sample, a higher pulse rate may lead to a better sampling of the sample position as a function of time, as the distance moved between each pulse is smaller.

The repetition rate of a laser subsystem can be increased by improving the laser medium, the pump system, and/or its driving electronics. Unfortunately, modifying a ultraviolet (UV) laser that is already operating at a predetermined repetition rate can require a significant investment of time and money to improve one or more of its constituent elements, which may only incrementally improve the repetition rate.

Therefore, a need arises for a practical, inexpensive technique to improve the repetition rate of a laser.

SUMMARY OF THE INVENTION

In general, a method of generating optimized pulses for a system is described. In this method, an input laser pulse can be optically split into a plurality of pulses using a ring cavity. The plurality of pulses can be grouped into pulse trains, wherein the pulse trains are of approximately equal energy and are approximately equally spaced in time. A set of the pulse trains can be transmitted as the pulses for the system, whereas a remainder of the pulse trains can be reflected back into the ring cavity.

A pulse multiplier can include a polarizing beam splitter, a wave plate, and a set of mirrors. The polarizing beam splitter receives an input laser pulse. The wave plate receives light from the polarized beam splitter and generates first and second sets of pulses. In one embodiment, the wave plate includes a half-wave plate, which can be set at 27.3678 degrees. In another embodiment, the wave includes a quarter-wave plate. Notably, the first set of pulses has a different polarization than the second set of pulses. The set of mirrors create the ring cavity, which includes the polarizing beam splitter and the wave plate. The polarizing beam splitter advantageously transmits the first set of pulses as an output of the pulse multiplier and reflects the second set of pulses back into the ring cavity.

The pulse multiplier can further include one or more lens for uniformly shaping the pulses in the ring cavity. In one embodiment, a plurality of lenses can be implemented with two image relay tubes.

In one embodiment, the mirror set can include a composite mirror. In another embodiment, the mirror set can create two ring cavities that share the polarizing beam splitter and the wave plate. In yet another embodiment, the mirror set can create two ring cavities connected in series, wherein each ring cavity includes its own polarizing beam splitter and wave plate.

Another embodiment of a pulse multiplier without a ring cavity is described. In this pulse multiplier, the polarizing beam splitter receives an input laser pulse and the wave plate (e.g. a quarter-wave plate) receives light from the polarizing beam splitter and generates a first set of pulses and a second set of pulses, the first set of pulses having a different polarization than the second set of pulses. A set of multi-surface reflecting components (e.g. a mirror and etalons) reflects the first and second sets of pulses back through the wave plate to the polarizing beam splitter. The polarizing beam splitter transmits the first set of pulses as an output of the pulse multiplier and reflects the second set of pulses back to the wave plate and the set of multi-surface reflecting components. The peak output power of the second set of pulses can be tunable to $\sin^2 \theta$.

Yet another embodiment of a pulse multiplier without a ring cavity is described. In this pulse multiplier, a first wave plate receives an input laser pulse and a polarizing beam splitter receives outputs of the first wave plate. A second wave plate receives a first set of pulses from the polarizing beam splitter. A first mirror reflects outputs from the second wave plate back through the second wave plate to the polarizing beam splitter. A third wave plate receives a second set of pulses from the polarizing beam splitter. A second mirror reflects outputs from the third wave plate back through the third wave plate to the polarizing beam splitter. Notably, the polarizing beam splitter transmits a third set of pulses from the second wave plate combined with a fourth set of pulses from the third wave plate to generate an output of the pulse multiplier. The polarizing beam splitter also reflects a fifth set of pulses from the second wave plate back to the second wave plate and the first mirror, and reflects a sixth set of pulses back to the third wave plate and the second mirror. In one embodiment, the first wave plate includes a half-wave plate, and the second and third wave plates include quarter-wave plates.

Any of the above-described pulse multipliers can be included in a wafer inspection system, a patterned wafer system, a mask inspection system, or a metrology system.

The pulse multiplier can inexpensively reduce the peak power per pulse while increasing the number of pulses per second with minimal total power loss. The pulse multiplier can advantageously enable high speed inspection and metrology with off-the-shelf lasers.

BRIEF DESCRIPTION OF THE DRAWINGS

FIGS. 3A, 3B, and 3C illustrate lens configurations in a pulse multiplier for 1 lens, 2 lenses, and 4 lenses, respectively.

FIG. 9A illustrates a pulse multiplier including two adjacent ring cavities connected in series.

FIG. 9B illustrates a pulse multiplier including a semi-nested ring cavity, thereby allowing the sharing of some components between two ring cavities.

DETAILED DESCRIPTION OF THE DRAWINGS

In accordance with one aspect of an improved pulse multiplier, each laser pulse can be optically split into a plurality of pulses, which are grouped into pulse trains. In one embodiment, these pulse trains may be of approximately equal energy and may be approximately equally spaced in time. This splitting of the laser pulse can provide a practical and inexpensive solution to the above-noted problems with minimal energy losses.

Figure 1:
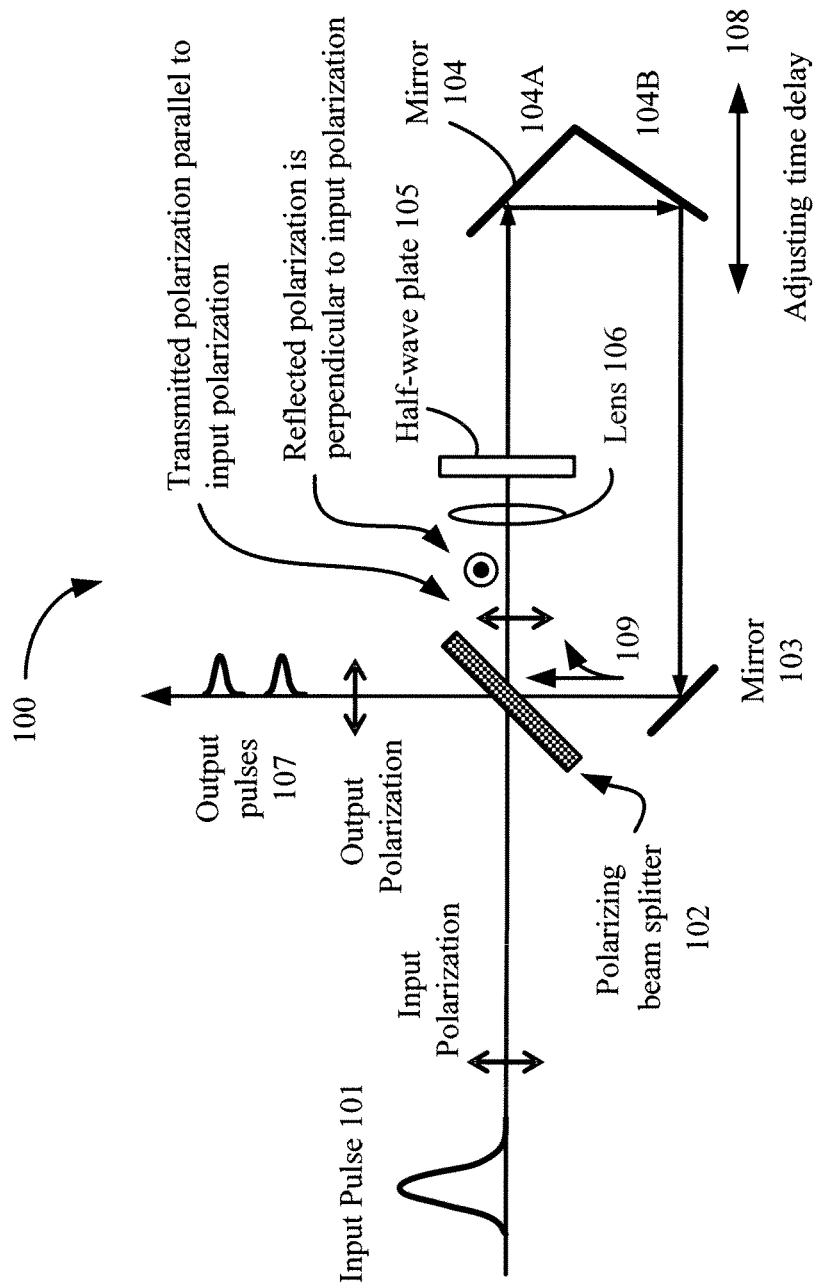
FIG. 1 illustrates an exemplary pulse multiplier configured to generate pulse trains from each input laser pulse.

FIG. 1 illustrates an exemplary pulse multiplier 100 configured to generate pulse trains from each input pulse 101. Input pulse 101 impinges on a polarizing beam splitter 102, which because of the input polarization of input pulse 101, transmits all of its light to a lens 106. Thus, the transmitted polarization is parallel to the input polarization of input pulse 101. Lens 106 focuses and directs the light of input pulse 101 to a half-wave plate 105. In general, a wave plate can shift the phases between perpendicular polarization components of a light wave. For example, a half-wave plate receiving linearly polarized light can generate two waves, one wave parallel to the optical axis and another wave perpendicular to the optical axis. In half-wave plate 105, the parallel wave can propagate slightly slower than the perpendicular wave. Half-wave plate 105 is fabricated such that for light exiting, one wave is exactly half of a wavelength delayed (180 degrees) relative to the other wave. Moreover, the combination of the two waves is orthogonally polarized compared to the light entering the plate.

Thus, half-wave plate 105 can generate pulse trains from each input pulse 101. The normalized amplitudes of the pulse trains are: $\cos 2\theta$ (wherein $\theta$ is the angle of half-wave plate 105), $\sin^2 2\theta$, $\sin^2 2\theta \cos 2\theta$, $\sin^2 2\theta \cos^2 2\theta$, $\sin^2 2\theta \cos^3 2\theta$, $\sin^2 2\theta \cos^4 2\theta$, $\sin^2 2\theta \cos^5 2\theta$, etc. Notably, the total energy of the pulse trains from a laser pulse can be substantially conserved traversing half-wave plate 105.

The sum of the energy from the odd terms generated by half-wave plate 105 is equal to:

$$(\cos 2\theta)^2 + (\sin^2 2\theta \cos 2\theta)^2 + (\sin^2 2\theta \cos^3 2\theta)^2 + (\sin^2 2\theta \cos^5 2\theta)^2 + (\sin^2 2\theta \cos^7 2\theta)^2 + (\sin^2 2\theta \cos^9 2\theta)^2 + \ldots = \cos^2 2\theta \sin^4 2\theta (\cos^2 2\theta + \cos^6 2\theta + \cos^{10} 2\theta + \ldots) = 2\cos^2 2\theta/(1+\cos^2 2\theta)$$

In contrast, the sum of the energy from the even terms generated by half-wave plate 105 is equal to:

$$(\sin^2 2\theta)^2 + (\sin^2 2\theta \cos^2 2\theta)^2 + (\sin^2 2\theta \cos^4 2\theta)^2 + (\sin^2 2\theta \cos^6 2\theta)^2 + (\sin^2 2\theta \cos^8 2\theta)^2 + (\sin^2 2\theta \cos^{10} 2\theta)^2 + \ldots = \sin^4 2\theta(1+\cos^4 2\theta+\cos^8 2\theta+\cos^{12} 2\theta+ \ldots) = \sin^2 2\theta/(1+\cos^2 2\theta)$$

In accordance with one aspect of pulse multiplier 100, the angle $\theta$ of half-wave plate 105 can be determined (as shown below) to provide that the odd term sum is equal to the even term sum.

$$2\cos^2 2\theta = \sin^2 2\theta$$

$$\cos^2 2\theta = 1/3$$

$$\sin^2 2\theta = 2/3$$

$$\theta = 27.3678 \text{ degrees}$$

Referring back to FIG. 1, the light exiting half-wave plate 105 is reflected by mirrors 104 and 103 back to polarizing beam splitter 102. Thus, polarizing beam splitter 102, lens 106, half-wave plate 105, and mirrors 104 and 103 form a ring cavity configuration. The light impinging on polarizing beam splitter 102 after traversing the ring cavity has two polarizations as generated by half-wave plate 105. Therefore, polarizing beam splitter 102 transmits some light and reflects other light, as indicated by arrows 109. Specifically, polarizing beam splitter 102 transmits the light from mirror 103 having the same polarization as input pulse 101. This transmitted light exits pulse multiplier 100 as output pulses 107. The reflected light, which has a polarization perpendicular to that of input pulse 101, is re-introduced into the ring cavity (pulses not shown for simplicity).

Notably, these re-introduced pulses can traverse the ring in the manner described above with further partial polarization switching by half-wave plate 105 and then light splitting by polarizing beam splitter 102. Thus, in general, the above-described ring cavity is configured to allow some light to exit and the rest of the light (with some minimal losses) to continue around the ring. During each traversal of the ring (and without the introduction of additional input pulses), the energy of the total light decreases due to the light exiting the ring as output pulses 107.

Periodically, a new input pulse 101 is provided to pulse multiplier 100. In one embodiment, for a 125 MHz laser input, 0.1 nanosecond (ns) laser pulses result. Note that the size of the ring, and thus the time delay of the ring, can be adjusted by moving mirror 104 along the axis indicated by arrows 108.

The ring cavity length may be slightly greater than, or slightly less than, the nominal length calculated directly from the pulse interval divided by the multiplication factor. This results in the pulses not arriving at exactly the same time as the polarized beam splitter and slightly broadens the output pulse. For example, when the input pulse repetition rate is 125 MHz, the cavity delay would nominally be 4 ns for a frequency multiplication by 2. In one embodiment, a cavity length corresponding to 4.05 ns can be used so that the multiply reflected pulses do not arrive at exactly the same time as an incoming pulse. Moreover, the 4.05 ns cavity length for the 125 MHz input pulse repetition rate can also advantageously broaden the pulse and reduce pulse height. Other pulse multipliers having different input pulse rates can have different cavity delays.

Notably, polarizing beam splitter 102 and half-wave plate 105 working in combination generate even and odd pulses, which diminish for each round traversed inside the ring. These even and odd pulses can be characterized as providing energy envelopes, wherein an energy envelope consists of an even pulse train (i.e. a plurality of even pulses) or an odd pulse train (i.e. a plurality of odd pulses). In accordance with one aspect of pulse multiplier 100, these energy envelopes are substantially equal.

Figure 2A:
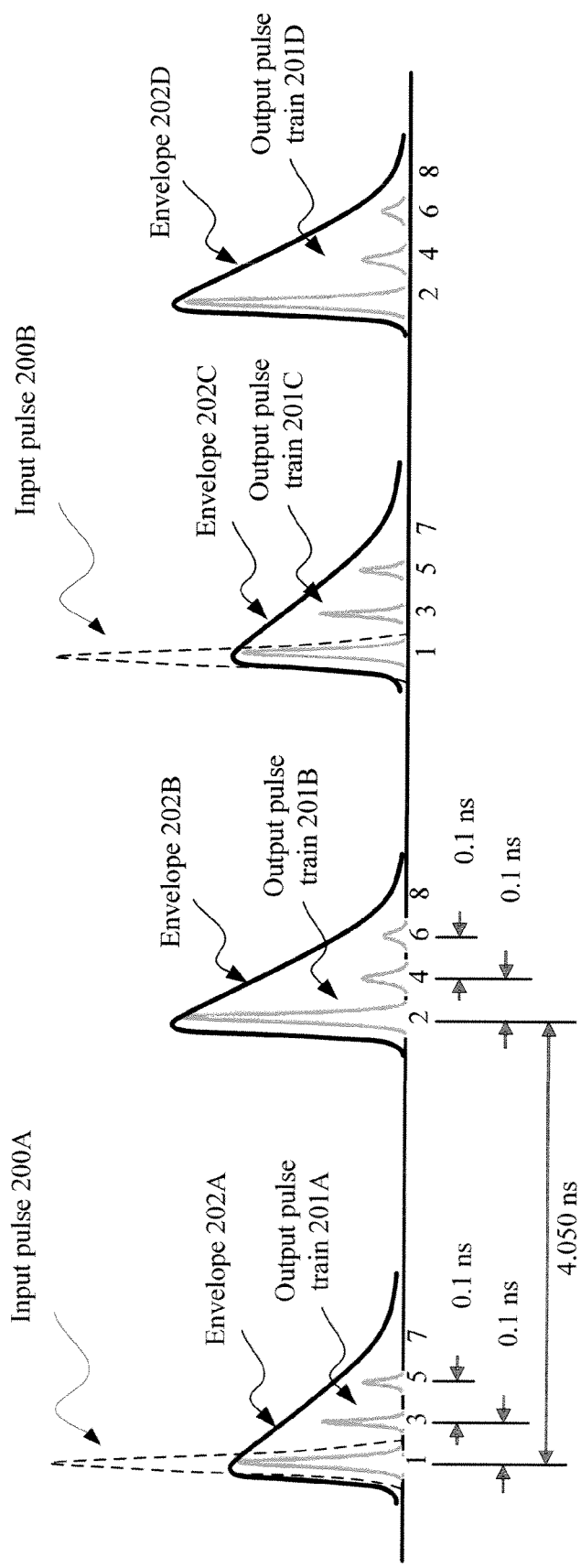
FIG. 2A illustrates exemplary energy envelopes output by the pulse multiplier of FIG. 1. Each energy envelope includes an output pulse train.

FIG. 2A illustrates exemplary energy envelopes 202A, 202B, 202C, and 202D, which consist of output pulse trains 201A, 201B, 201C, and 201D, respectively. As shown, output pulse trains exemplify the above-described embodiment. That is, time delays between odd/even pulses is 0.1 ns and time delays between associated pulses (i.e. 1→2, 3→4, 5→6) of adjacent power envelopes is 4.050 ns. Notably, the time between odd/even pulses is far enough apart so that they can be incoherently added (and conversely that they do not coherently interfere with one another).

Figure 2B:
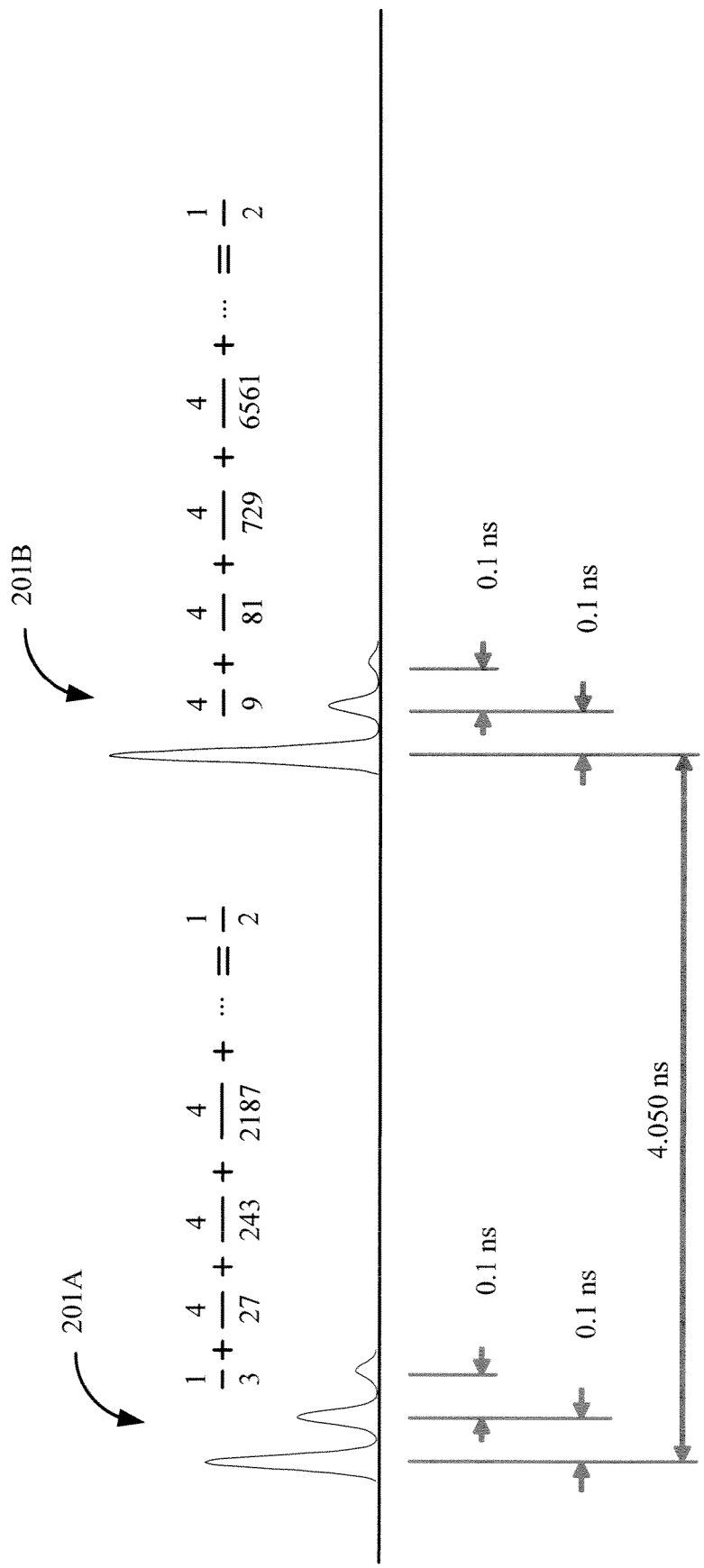
FIG. 2B illustrates that the pulse multiplier of FIG. 1 can double the original repetition pulse rate while reducing peak power and ensuring energy balancing outputs.

Note that original pulses 200A and 200B are not part of power envelopes 202A and 200C, but are shown for context. Specifically, polarizing beam splitter 102 and half-wave plate 105 use original pulses 200A and 200B to generate output pulse trains 201A-201D. FIG. 2B illustrates that the normalized sum of the individual pulses in each of pulse trains 201A and 201B is equal to ½ and the normalized sum of pulse trains 201A and 201B is equal to 1. Thus, the configuration described for pulse multiplier 100 can double the original repetition pulse rate while reducing peak power and ensuring energy balancing outputs.

Notably, referring back to FIG. 1, during each traversal of the ring, lens 106 can uniformly shape the light pulses. This uniformity allows pulses to be added (for example, as shown in FIG. 2B) with consistent results of predetermined size envelopes (for example, as shown in FIG. 2A). Thus, lens 106 can advantageously maintain high beam quality for pulse multiplier 100.

Note that although only one lens, i.e. lens 106, is shown in pulse multiplier 100, other embodiments may include more lenses. The purpose of having at least one lens in the above-described pulse multiplier is to ensure uniform Gaussian beam shape at specific points in the beam relay, i.e. to refocus the beam waist to compensate for the length of the ring cavity. FIGS. 3A, 3B, and 3C illustrate lens configurations for 1 lens, 2 lenses, and 4 lenses, respectively. Note that the number of lenses refers specifically to the number of lenses in the ring cavity. Therefore, for example, configuration 301 (FIG. 3A) has one lens forming part of the ring cavity, but in fact requires an additional two lenses outside the ring cavity to form collimated beams. Note that horizontal and vertical lines in the Gaussian beam relays shown in FIGS. 3A-3C indicate image planes, which is known to those skilled in the art, whereas diagonal lines refer to either mirrors or the polarizing beam splitter. For example, in configuration 302 (FIG. 3B), three image planes 304 are provided. FIG. 3C illustrates a configuration 303 having 4 lenses, which forms a telescopic pair having a magnification of 1×. Configuration 303 (like configuration 302) also generates two internal images. However, configuration 303 does not require mirrors between the lens pair forming the telescope. Therefore, configuration 303 could be built using two image relay tubes with adjustment mirrors between the tubes, thereby simplifying component alignment and component assembly compared to configuration 302, for example.

Generally, a 2 lens configuration (also called a lens doublet) can provide beam quality at the refocused beam waist than a 1 lens configuration. However, the number of lenses in the lens configuration may vary based on the requirements of a specific application. Alternative pulse multiplier embodiments may include using one or more curved focusing mirrors instead of, or in addition to, the one or more lenses. In one embodiment, the laser beam diameter is expanded to about 10 mm wide before entering the ring cavity and therefore does not need refocusing. In this embodiment having what can be characterized as a wide beam, both lenses and curved mirrors can be eliminated.

Figure 4:
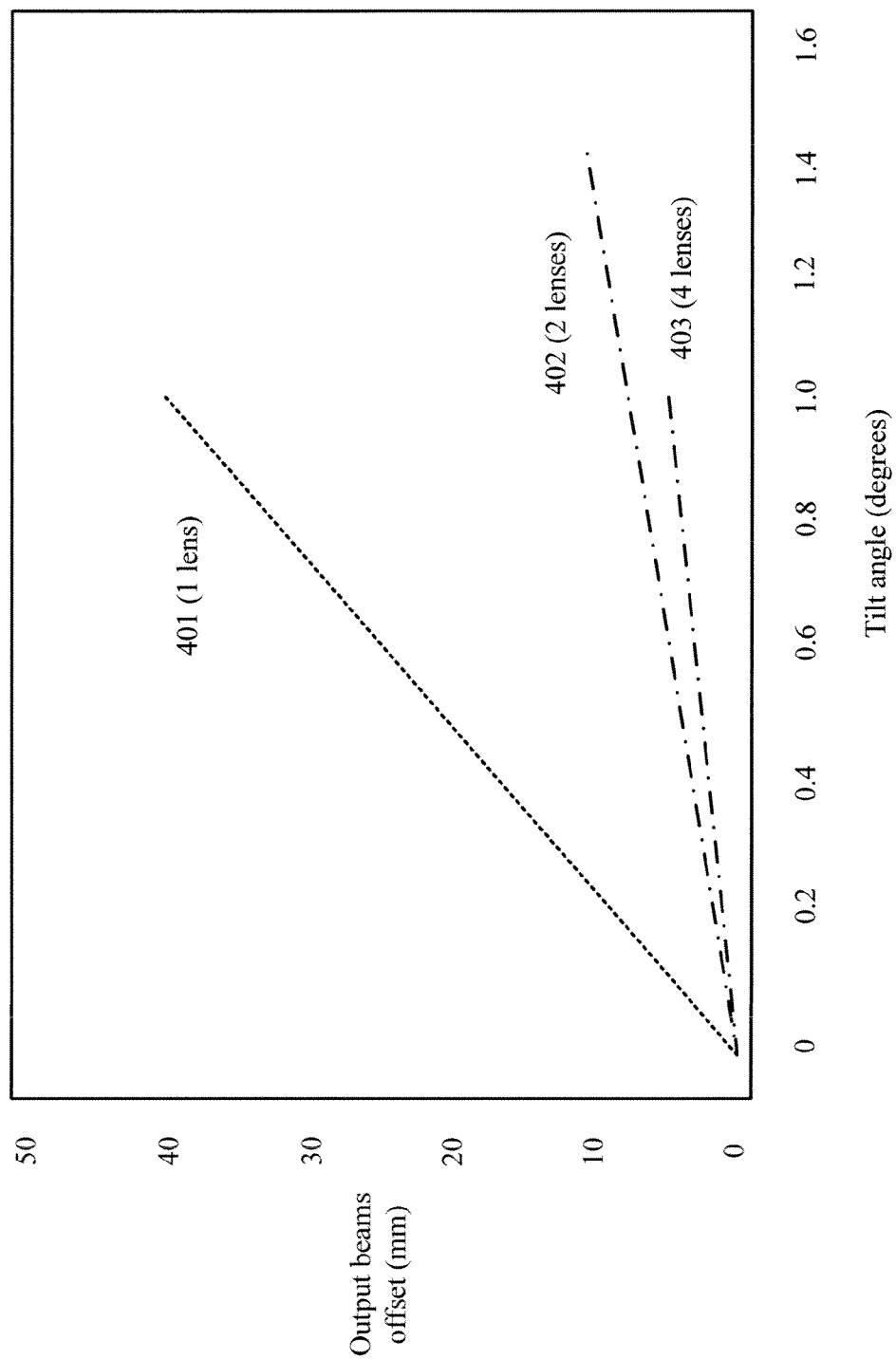
FIGS. 4 and 5 illustrate how mirror tilt can affect output beams offset.
Figure 5:
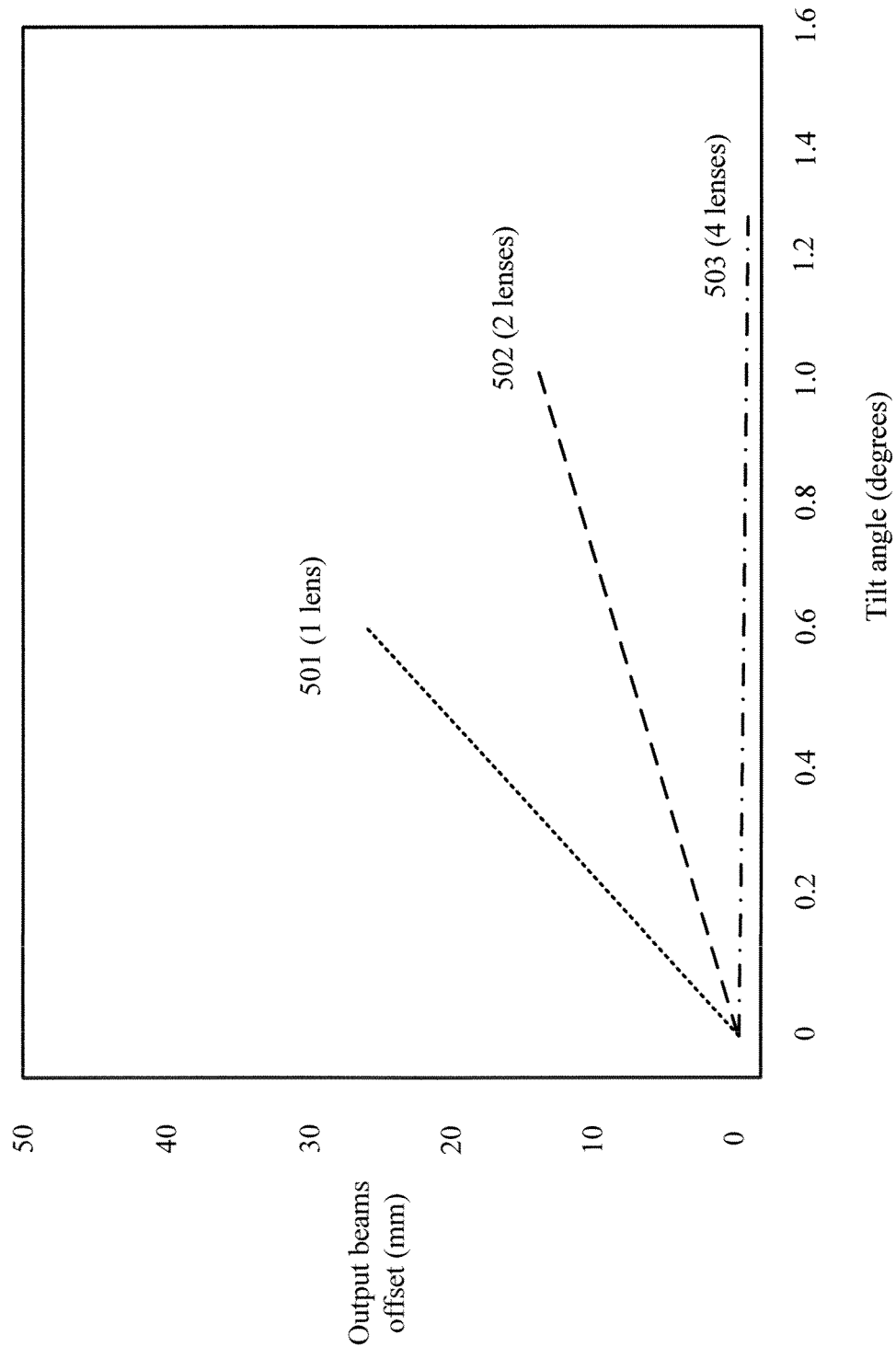

FIGS. 4 and 5 illustrate how mirror tilt can affect output beams offset (in millimeters). Note that referring back to FIG. 1, the function provided by mirror 104 can also be performed using two mirrors 104A and 104B, wherein mirror 104A can be characterized as a first corner mirror (when traversing the ring cavity) and mirror 104B can be characterized as a second corner mirror. FIGS. 4 and 5 illustrate the sensitivity of first and second corner mirrors, respectively, based on mirror tilt. Three lens configurations are shown: 1 lens configuration (401)(501), 2 lens configuration (402)(502), and 4 lens configuration (403)(503). FIG. 4 indicates that the 1 lens configuration has significantly more sensitivity to mirror tilt than the 2 or 4 lens configurations (which are relatively close in sensitivity). FIG. 5 indicates that the 4 lens configuration significantly reduces sensitivity to mirror tilt compared to either the 1 or 2 lens configuration.

Note that some advantages can be realized by using composite mirror 104 rather than separate mirrors 104A and 104B. For example, pre-assembly of composite mirror 104 to provide an exact 90 degree angle can facilitate easier field assembly than aligning individual mirrors 104A and 104B. Moreover, composite mirror 104 can provide a return direction that is independent of the angle of the two mirrors. Therefore, composite mirror 104 can be rotated while still ensuring that light will always be reflected in parallel to input light. As a result, composite mirror 104 may provide some performance advantages to separate mirrors 104A and 104B. Composite mirror 104 can be implemented using reflecting prisms, glass blocks, machined mirrors, or other suitable materials.

Figure 6:
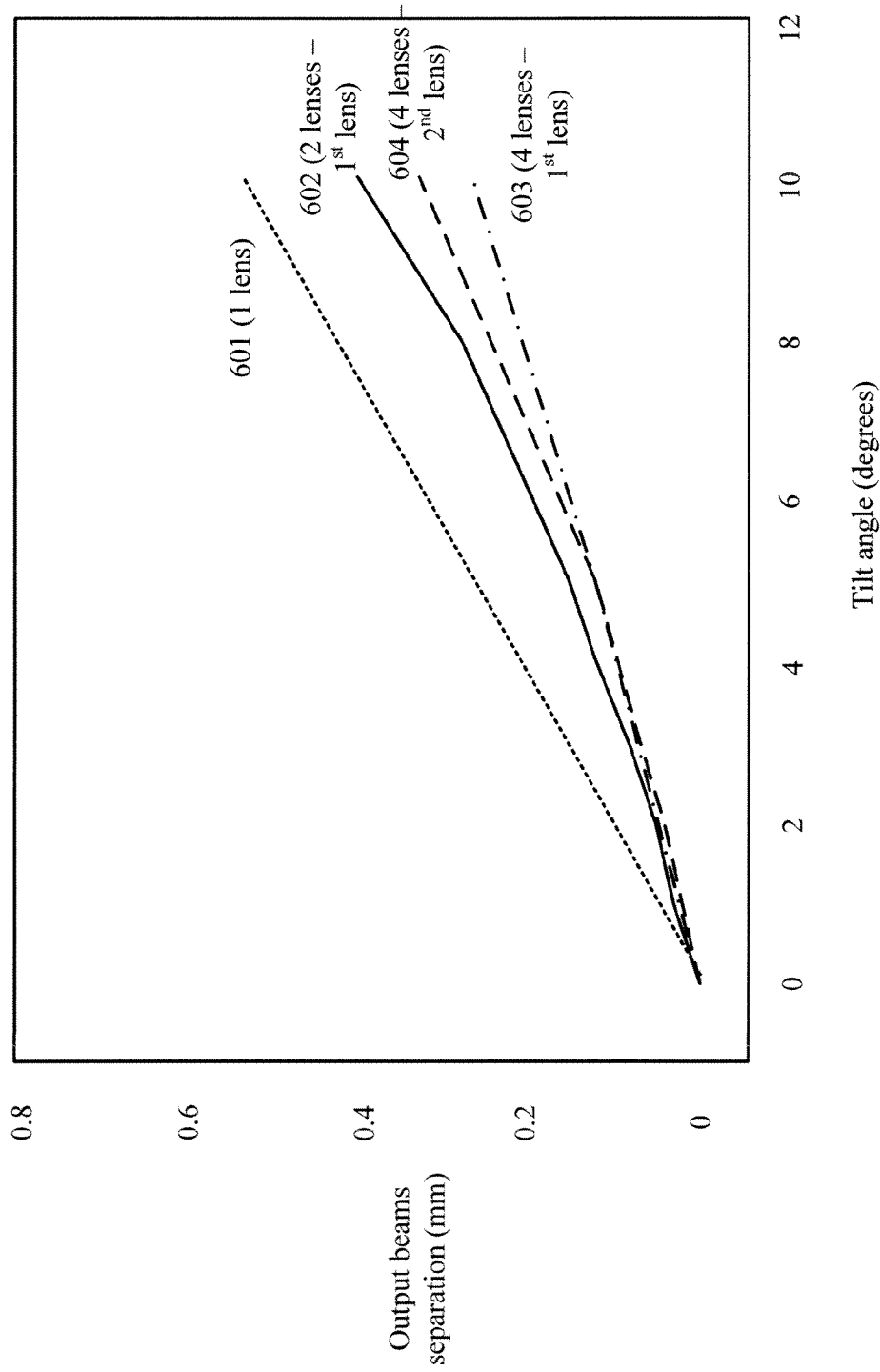
FIG. 6 illustrates how lens tilt can affect output beams offset.

FIG. 6 illustrates how lens tilt can affect output beams offset (in millimeters). The sensitivities of four different lenses are shown in FIG. 6: 1 lens (601), $1^{st}$ of 2 lenses (602), $1^{st}$ of 4 lenses (603), and $2^{nd}$ of 4 lenses (604). As shown, a one lens configuration exhibits moderately more sensitivity to tilt than any other configuration as the tilt angle increases.

Figure 7:
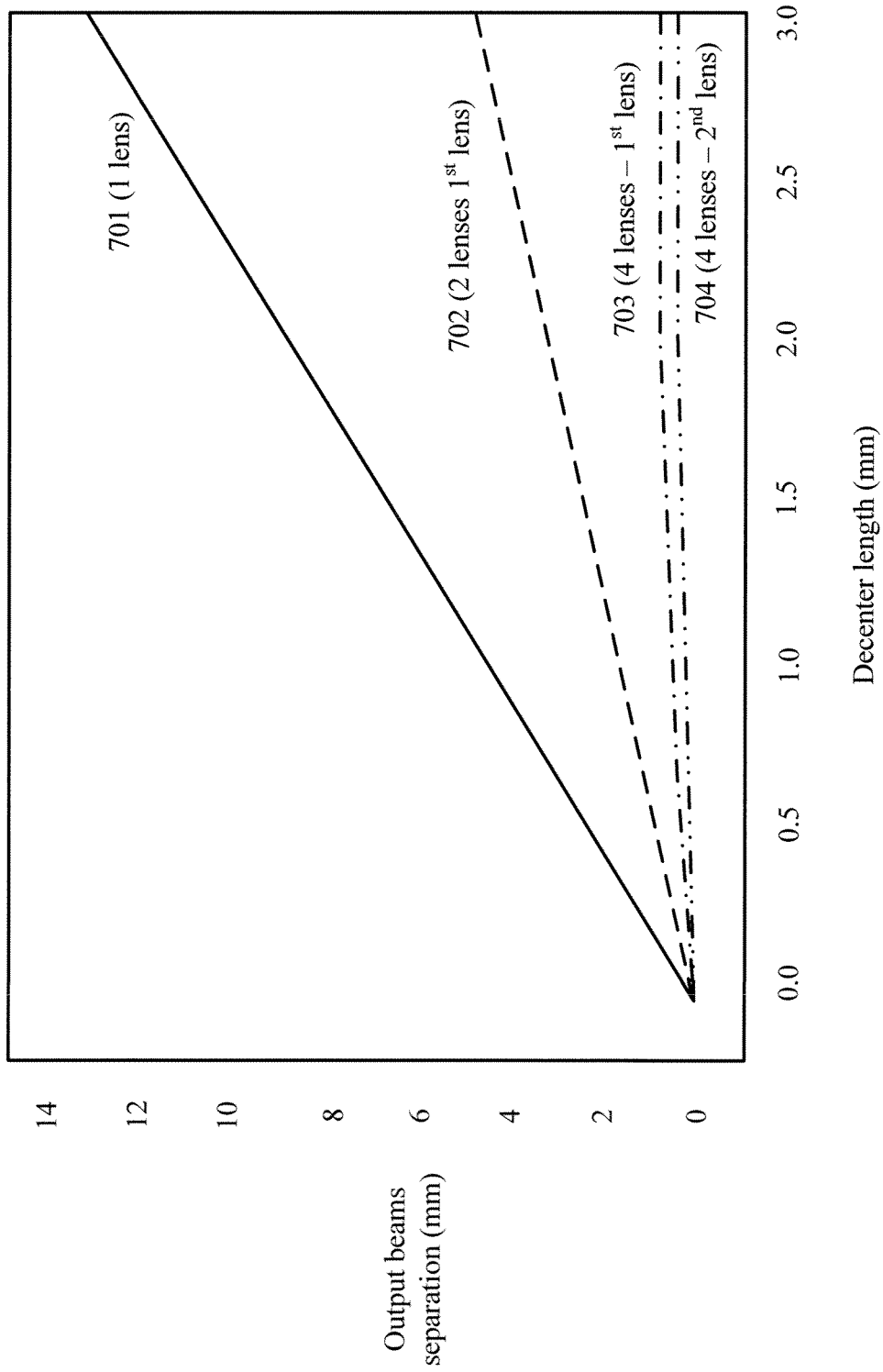
FIG. 7 illustrates how lens decenter misalignment can affect output beams offset.

FIG. 7 illustrates how lens decenter misalignment can affect output beams offset (both in millimeters). The sensitivities of four different lenses are shown in FIG. 7: 1 lens (701), 1$^{st}$ of 2 lenses (702)], 1$^{st}$ of 4 lenses (703), and 2$^{nd}$ of 4 lenses (704). As shown, a lens configuration exhibits significantly more sensitivity to decenter misalignment than the 4 lens configuration (either 1$^{st}$ or 2$^{nd}$ lenses) and moderately more sensitivity to decenter misalignment than the 2 lens configuration.

Tables 1 and 2 provide exemplary data on how the beam splitter extinction ratio and polarization can affect energy efficiency for 2 and 4 lenses. Note that Tables 1 and 2 assume (1) an input beam is in perfect P-polarization, (2) high-reflector (HR) coating mirrors are Rp: 99.89%, Rs: 99.95%, (3) anti-reflective (AR) lenses are R: 0.2%, 4 lenses (8 surfaces), (4) the first reflection is included in the calculation, and (5) the half-wave plate is not fixed at 27.36 degrees.

The beam splitter extinction ratio is the ratio of the transmission of the wanted component to the unwanted component (i.e. for a polarizer, the ratio of the transmitted light to the reflected light). Notably, the polarization purity is predominantly a function of the beam splitter extinction ratio. In one embodiment, an additional polarizer can be added at the output of the pulse multiplier to improve polarization purity with a small loss.

The best angle for the half-wave plate to reach equal pulse-to-pulse energy will depend on extinction ratio and other cavity losses. Tables 1 and 2 consider examples using a finite extinction ratio polarizer and non-ideal component transmissions and reflectivities, and estimate the optimum waveplate angle requirement.

TABLE 1

Extinction Ratios for 2 Lenses

| Beamsplitter Extinction Ratio Tp/Ts | Energy Efficiency % | Polarization Purity P/S | Half-Wave Plate Angle |
| --- | --- | --- | --- |
| 100:1 | 96.21 | 99.73 | 26.85 |
| 150:1 | 97.3 | 150.27 | 26.29 |
| 200:1 | 97.6 | 200.4 | 26.15 |
| 500:1 | 98.0 | 500.07 | 26.45 |

TABLE 2

Extinction Ratios for 4 Lenses

| Beamsplitter Extinction Ratio Tp/Ts | Energy Efficiency % | Polarization Purity P/S | Half-Wave Plate Angle |
| --- | --- | --- | --- |
| 100:1 | 95.16 | 99.93 | 26.35 |
| 150:1 | 95.12 | 148.68 | 27.45 |
| 200:1 | 96.4 | 200.6 | 26.05 |
| 500:1 | 96.5 | 498.75 | 26.45 |

In one preferred embodiment, the number of components in the pulse multiplier can be minimized. Specifically, for even small losses associated with each component, such as those shown in Table 1 above, each traversal of light through the ring cavity can minimally degrade performance by a predetermined amount. Therefore, minimizing components in that ring cavity can provide one way of minimizing performance degradation. For example, each lens has two surfaces, each surface having a predetermined loss. Therefore, a 1- or 2-lens configuration (with 2 and 4 surfaces, respectively) may provide better performance than a 4-lens configuration (with 8 surfaces) (assuming lenses of equivalent quality).

Figure 8:
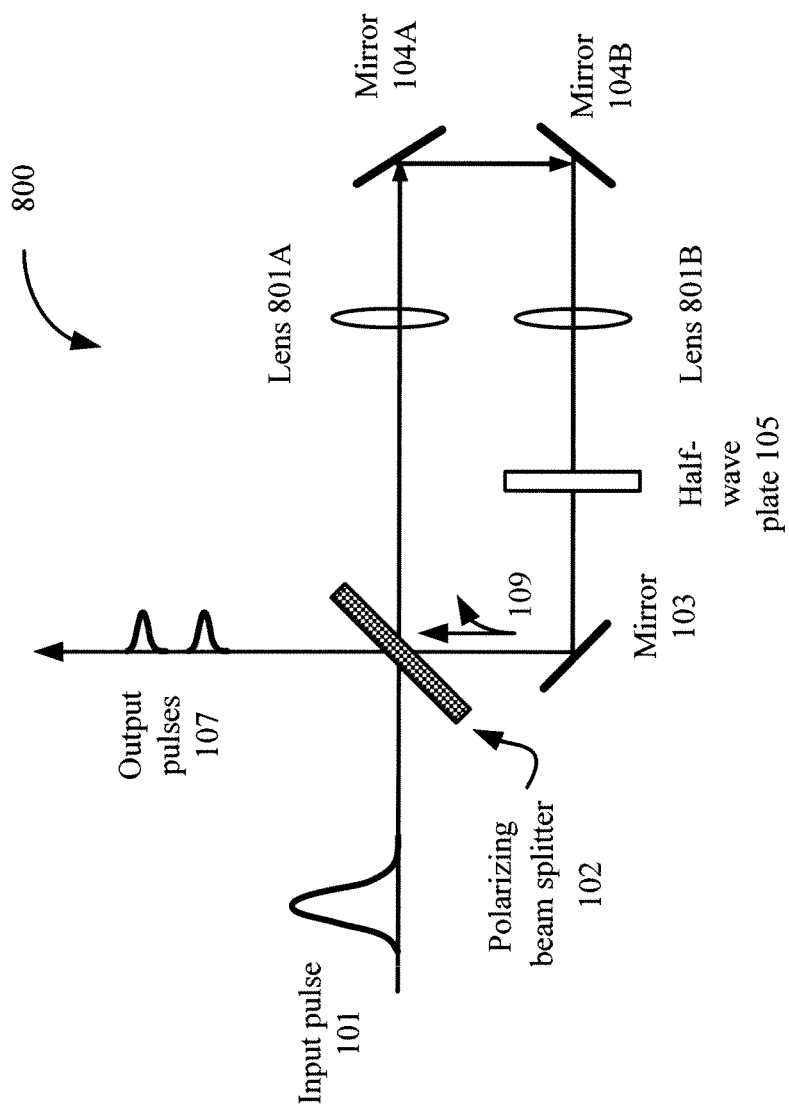
FIG. 8 illustrates an exemplary embodiment of a pulse multiplier including two lenses.

FIG. 8 illustrates an exemplary embodiment of a pulse multiplier 900 including two lenses 801A and 801B. Note also that mirror 104 (FIG. 1) is now separate mirrors 104A and 104B. In this embodiment, lens 801A is positioned between polarizing beam splitter 102 and mirror 104A, whereas lens 801B, half-wave plate 105 and mirror 103 are positioned between mirror 104B and polarizing beam splitter 102. This configuration and any others having one ring cavity and any number of lenses can provide a 2× rate increase in output pulses 107 compared to the rate of input pulse 101.

In one embodiment, two cavities of different lengths can be used in series to multiply the pulse rate by four or more. For example, FIG. 9A illustrates a pulse multiplier including two ring cavities 900A and 900B in series (note that ring cavities 900A and 900B could be adjacent on the same plane, as shown, or place one on top of another), each ring cavity including a polarizing beam splitter 901, a half-wave plate 902, and mirrors 903 (lens or lenses not shown for simplicity).

FIG. 9B illustrates a pulse multiplier including a semi-nested ring cavity, thereby allowing the sharing of some components between two ring cavities. For example, in this embodiment, polarizing beam splitter 911, half-wave plate 912, and mirror 913' can be shared by both ring cavities 910A and 910B (ring cavity 910B having two portions, one portion nested within ring cavity 910A and the other portion outside ring cavity 910A). Note that mirrors 913 form part of their respective ring cavities (lens or lenses, which can be placed using conventional practice, not shown for simplicity). As shown in FIG. 9B, after the light leaves ring cavity 910A, the light first traverses the portion of ring cavity 910B outside ring cavity 910A, then traverses the portion of ring cavity 910 nested in ring cavity 910A. In one embodiment, the second ring cavity 900B/910B can have substantially half the cavity length of the first ring cavity (900A/910A) to provide a pulse repetition rate multiplied by four.

Notably, the pulse multipliers in FIGS. 9A and 9B can provide a 4× rate increase compared to the input pulse. Other embodiments can include more ring cavities, wherein each ring increases the rate (e.g. 3 ring cavities provides 8×, 4 ring cavities provides 16×, etc.).

Note that although a half-wave plate is included in the above-described pulse multiplier embodiments, other wave plates can be used in other embodiments. That is, one or more wave plates of different retardances may be used instead of a single half-wave plate. For example, a half-wave plate can be replaced by a quarter-wave plate or a combination of a half-wave and a quarter-wave plate depending on the desired multiplication factor and whether a train of equal strength pulses is required or if a train of decaying pulse amplitudes is required.

In one embodiment of a pulse multiplier, at least one ring cavity can include 2 wave plates. In this case, the first wave plate can provide a phase delay of δ1 at angle θ1 and the second wave plate can provide a phase delay of δ2 at angle θ2. The electric field of the input laser pulse ($E_x$, $E_y$) can be determined by:

$$\begin{bmatrix} E'_x \\ E'_y \end{bmatrix} = \begin{bmatrix} \cos^2\theta_2 + e^{i\delta_2}\sin^2\theta_2 & (1 - e^{i\delta_2})\sin\theta_2\cos\theta_2 \\ (1 - e^{i\delta_2})\sin\theta_2\cos\theta_2 & \sin^2\theta_2 + e^{i\delta_2}\cos^2\theta_2 \end{bmatrix}$$

-continued $$\begin{bmatrix} \cos^2\theta_2 + e^{i\delta_2}\sin^2\theta_2 & (1-e^{i\delta_2})\sin\theta_2\cos\theta_1 \\ (1-e^{i\delta_2})\sin\theta_2\cos\theta_2 & \sin^2\theta_2 + e^{i\delta_2}\cos^2\theta_1 \end{bmatrix} \begin{bmatrix} E_x \\ E_y \end{bmatrix}$$

In one embodiment, the first phase plate can be set as a quarter-wave plate and the second phase plate as a half-wave plate, as indicated below.

$$\begin{bmatrix} E'_x \\ E'_y \end{bmatrix} = \begin{bmatrix} \cos^2\theta_2 & \sin\theta_2 \\ \sin\theta_2 & -\cos^2\theta_2 \end{bmatrix} \begin{bmatrix} \cos^2\theta_1 + i\sin^2\theta_1 & (1-i)\sin\theta_1\cos\theta_1 \\ (1-i)\sin\theta_1\cos\theta_1 & \sin^2\theta_1 + i\cos^2\theta_1 \end{bmatrix} \begin{bmatrix} E_x \\ E_y \end{bmatrix}$$

In one embodiment, the ring cavity can be aligned as described below. Initially, the pulse shape and timing can be observed using a photodiode and an oscilloscope to adjust the cavity length. Then, a camera located 1-2 m from the ring cavity exit can be used to detect the laser beam profile and location. At this time, the wave plate θ can be set to zero degrees. In this configuration, the pulse goes once around the ring cavity and exits with no significant reflected light from the polarized beam splitter being redirected to the ring cavity (and thus no rate increase should occur). Then the wave plate θ can be set to 45 degrees. In this configuration, the pulse should traverse the ring cavity twice and then exit. Specifically, insignificant transmission occurs through the polarized beam splitter after the first pass, but substantially complete transmission occurs after the second pass. Finally, the wave plate θ can be set to 27.3678 degrees so that the even and odd pulses energies will reach a balanced average power spatially upon exit from the cavity. Then, the optical components can be adjusted to ensure these two trace of light paths are of substantially the same size and arrive at the same location.

Moreover, pulse multipliers with ring cavities are capable of generating pulse trains with different amplitudes, should that feature be desired. For example, with an appropriate wave plate orientation, the second pulse could be stronger than the first pulse. Specifically, if the axis of the half-wave plate is oriented at an angle to the x axis (the plane containing the polarization vector of the incoming laser) greater than about 27.4 degrees, then the first pulse will be weaker than the second pulse. Alternative configurations can divide one pulse into a train of pulses of decreasing amplitude. Such a train could then repeat for each incoming laser pulse.

Figure 10:
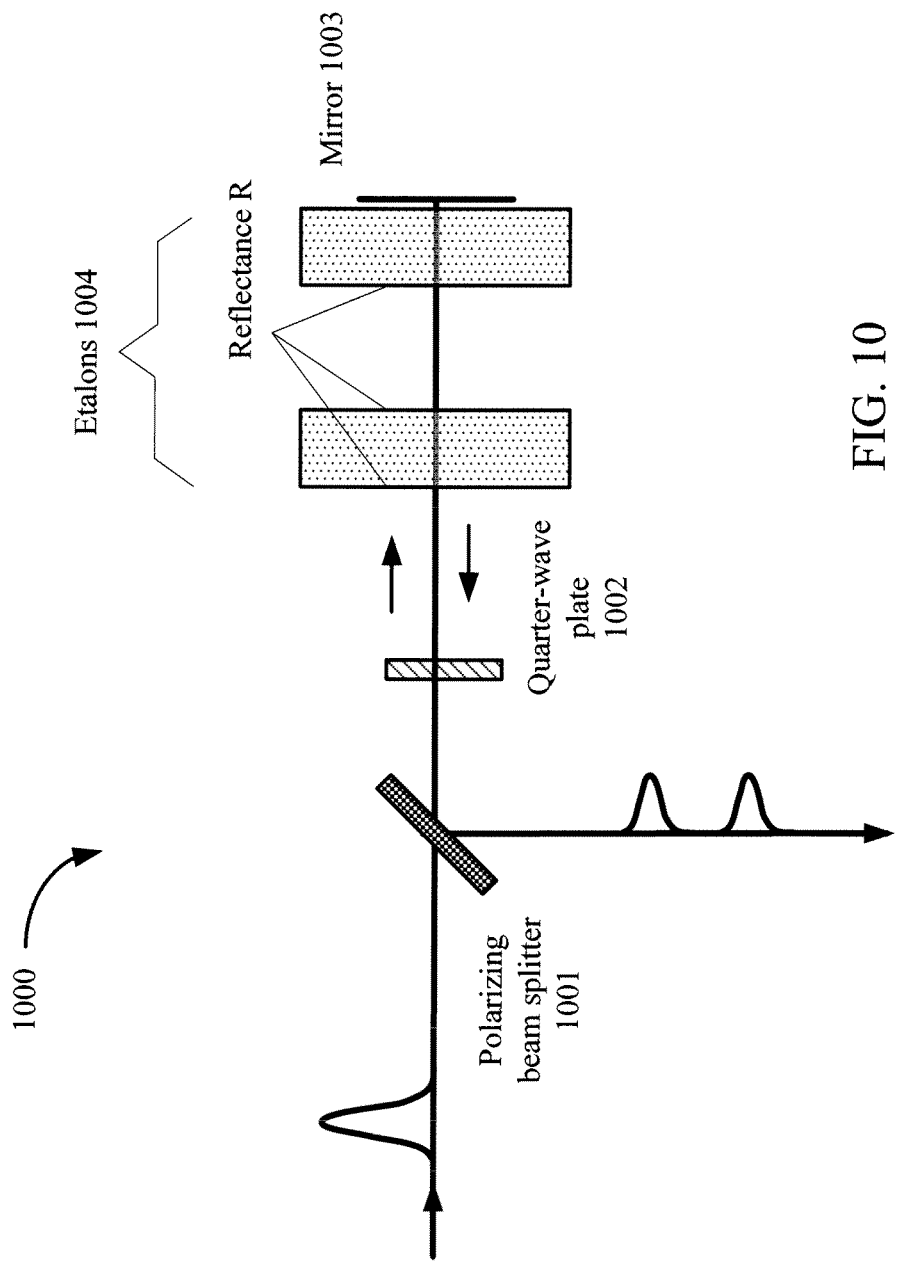
FIG. 10 illustrates a pulse multiplier including multi-surface reflection components.

Although pulse multipliers including ring cavities are described above, other pulse multiplier may include multi-surface reflection schemes without a ring cavity for generating pulses. For example, FIG. 10 illustrates a pulse multiplier 1000 including a polarizing beam splitter 1001, a quarter-wave plate 1002, a mirror 1003, and two etalon-like surfaces 1004. An etalon is typically formed by a transparent plate having two highly reflecting surfaces. In this embodiment, etalon-like surfaces 1004 can be formed with partially reflective surfaces. Note that in pulse multiplier 1000, the alignment of the optical components (and associated multiple surfaces) is relatively simple, although an interferometer may be needed for accurate alignment. Table 3 below indicates the exemplary reflectance R for various numbers (n) of surfaces. In general, optimized results are generated when $(1-R)^{2n}=R$, where R is the reflectance.

TABLE 3

Number of Surfaces vs. Reflection

| n | R |
|---|---|
| 1 | 0.382 |
| 2 | 0.276 |
| 3 | 0.222 |
| 4 | 0.188 |

Figure 11:
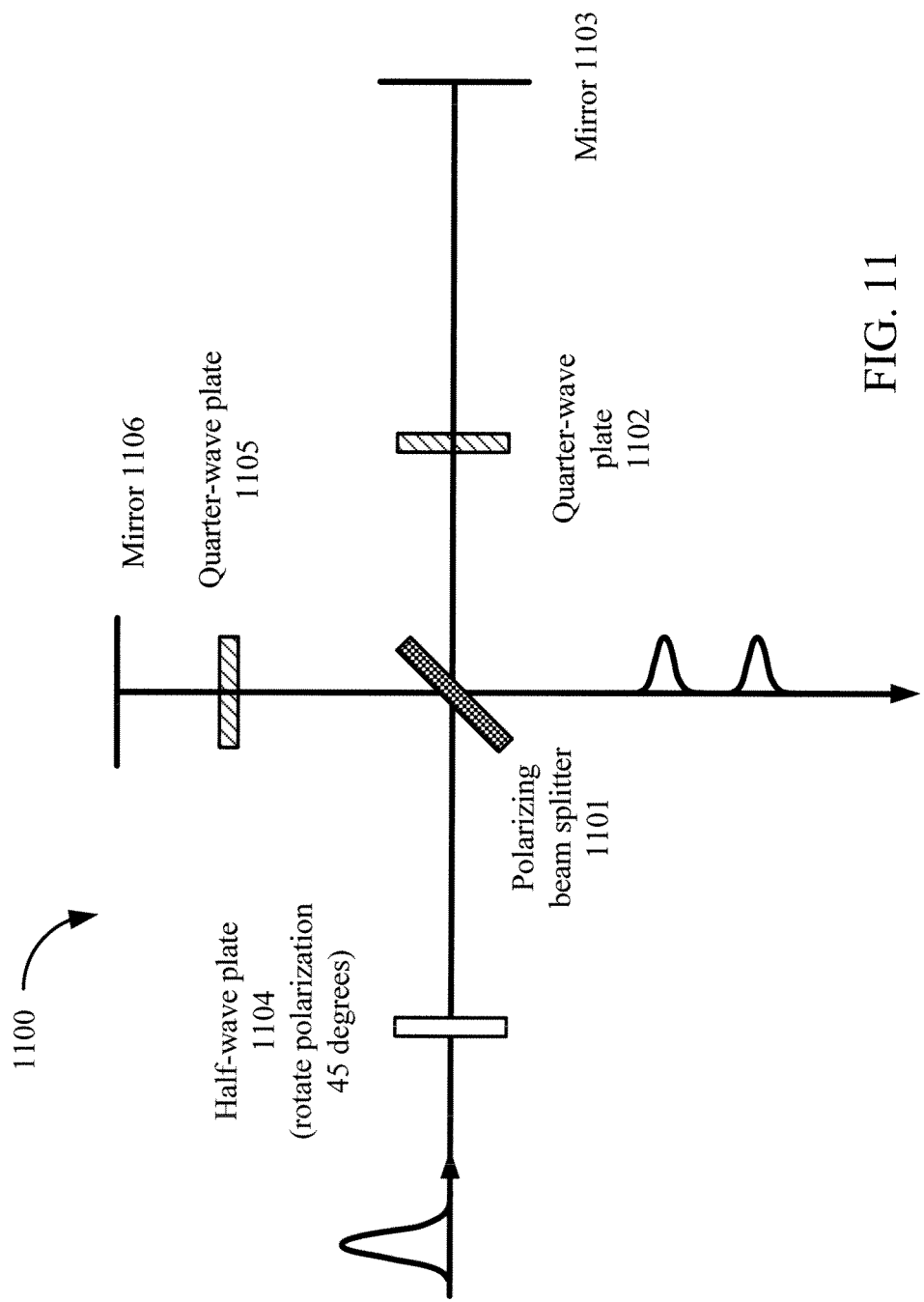
FIG. 11 illustrates an exemplary pulse multiplier that uses two combined beams to generate pulse outputs.

FIG. 11 illustrates an exemplary pulse multiplier 1100 that uses two combined beams to generate pulse outputs. Pulse multiplier 1100 includes a polarizing beam splitter 1101, two mirrors 1103 and 1106, two quarter-wave plates 1102 and 1105, and a half-wave plate 1104. In this configuration, polarizing beam splitter 1101 can direct light to both mirrors 1103 and 1106 via quarter-wave plates 1102 and 1105, respectively. The reflected light from mirrors 1103 and 1106 having the same polarization (again passing through quarter-wave plates 1105 and 1102) can be combined using polarizing beam splitter 1101. Pulse multiplier 1100 can only provide double the repetition rate of the input pulse, as shown. Note that for this configuration, an interferometer can be used to align pulse multiplier 1100.

Figure 12:
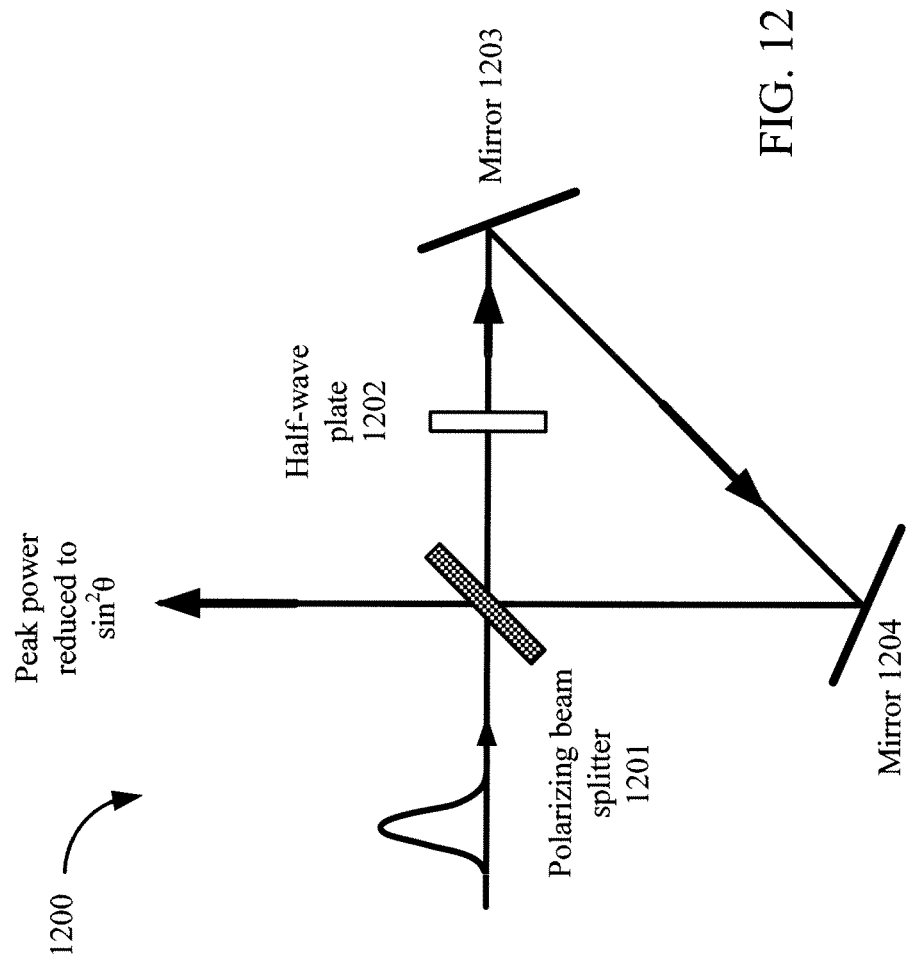
FIG. 12 illustrates an exemplary pulse multiplier that reduces the number of mirrors in the ring cavity compared to the pulse multiplier of FIG. 1.

FIG. 12 illustrates an exemplary pulse multiplier 1200 that reduces the number of mirrors in the ring cavity (e.g. compared to FIG. 1). Pulse multiplier 1200 includes a triangular ring cavity having a polarizing beam splitter 1201, two mirrors 1203 and 1204, and a half-wave plate 1202. In the configuration shown in FIG. 12, the first pulse is reflected from polarizing beam splitter 1201 and has a first polarization, whereas the second pulse is transmitted and has a second polarization different than the first polarization. The peak output power is tunable to $\sin^2\theta$. Note that for this configuration, an interferometer can be used to align pulse multiplier 1200.

Advantageously, inspection systems can include the above-described pulse multipliers. The inspection system can be a bright-field inspection system, a dark-field inspection system, or a system with both bright-field and dark-field modes. The inspection system can be configured to inspect semiconductor wafers or photo-lithography masks. Specifically, the inspection system may be configured to detect patterning defects on a patterned sample, or may be configured to detect particles, pits, or bumps on a patterned or un-patterned surface.

For example, the high-repetition rate laser pulses generated by the above-described pulse multipliers can be used in a flash-on-the-fly inspection system, wherein a single laser pulse illuminates a portion of a moving sample (such as a wafer or reticle) that is to be inspected and an image is acquired by a camera. Because each laser pulse is of short duration, the motion is effectively frozen and an un-blurred image is acquired. Advantageously, a higher repetition rate, as provided by the above-described pulse multipliers, can enable more images to be acquired per unit time, thereby allowing faster motion.

Figure 13:
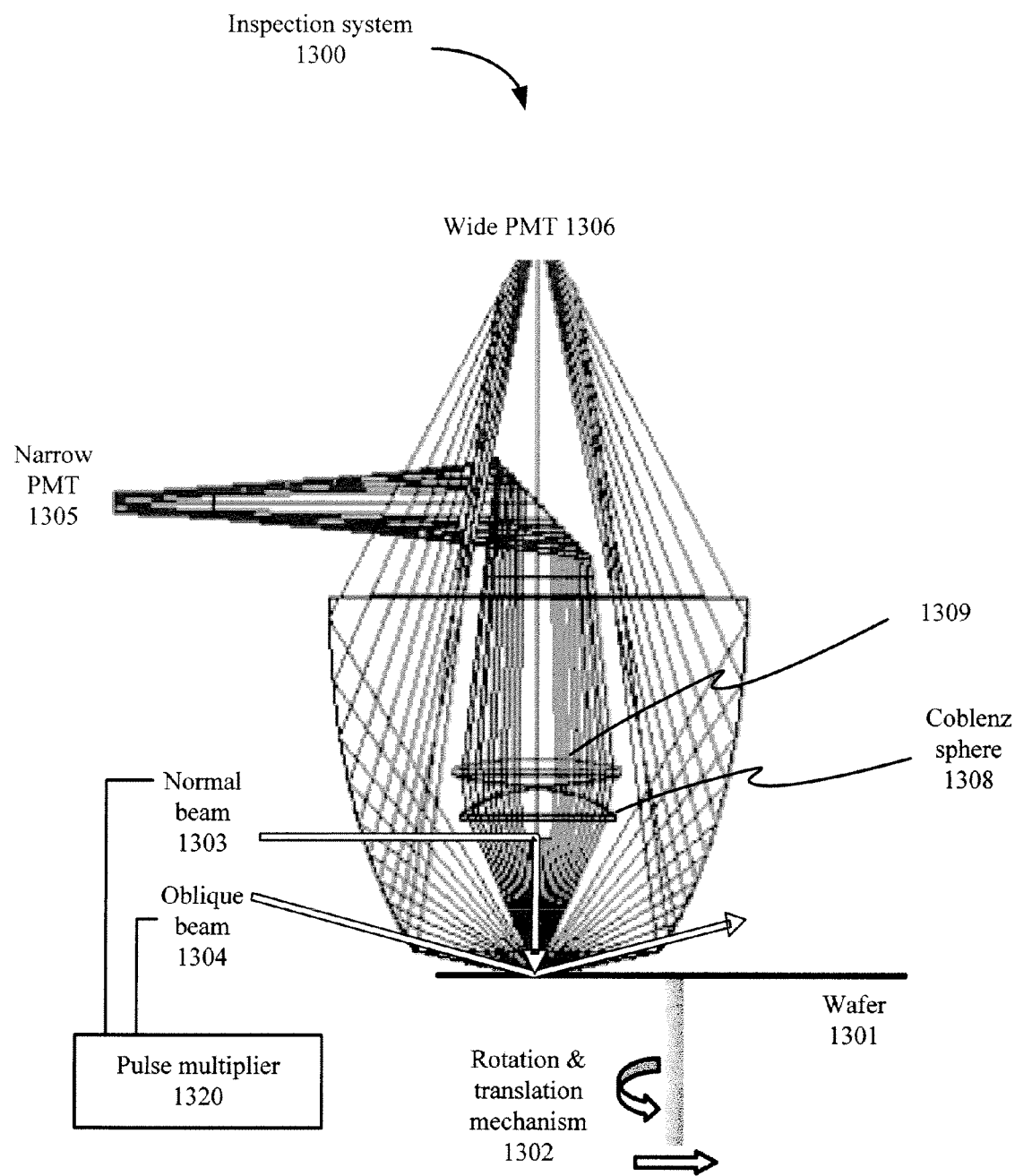
FIG. 13 illustrates an exemplary wafer inspection system including a pulse multiplier.

FIG. 13 illustrates an exemplary wafer inspection system 1300 including a pulse multiplier 1320. In system 1300, a waver 1301 can be rotated and translated using a mechanism 1302 to ensure the wafer's whole surface is scannable. Pulse multiplier 1302 can advantageously generate pulses for a normal beam 1303 and an oblique beam 1304 that are directed onto wafer 1301. The reflected incident light from wafer 1301 is then directed, for example using a Coblenz sphere 1308 and optics 1309, onto detectors (not shown for simplicity). System 1300 can provide both narrow and wide detection paths, e.g. including a narrow photo multiplier tube (PMT) 105 and a wide PMT 1306. U.S. Pat. No. 5,189,481, which issued to Jann et al. on Feb. 23, 1993, describes system 1300 in greater detail, and is incorporated by reference herein. Notably, pulse multiplier 1320 can multiply the pulses from a UV, DUV, or VUV laser. Pulse multiplier 1320 can advantageously increase the repetition rate while reducing the peak power of whatever laser is used.

Figure 14:
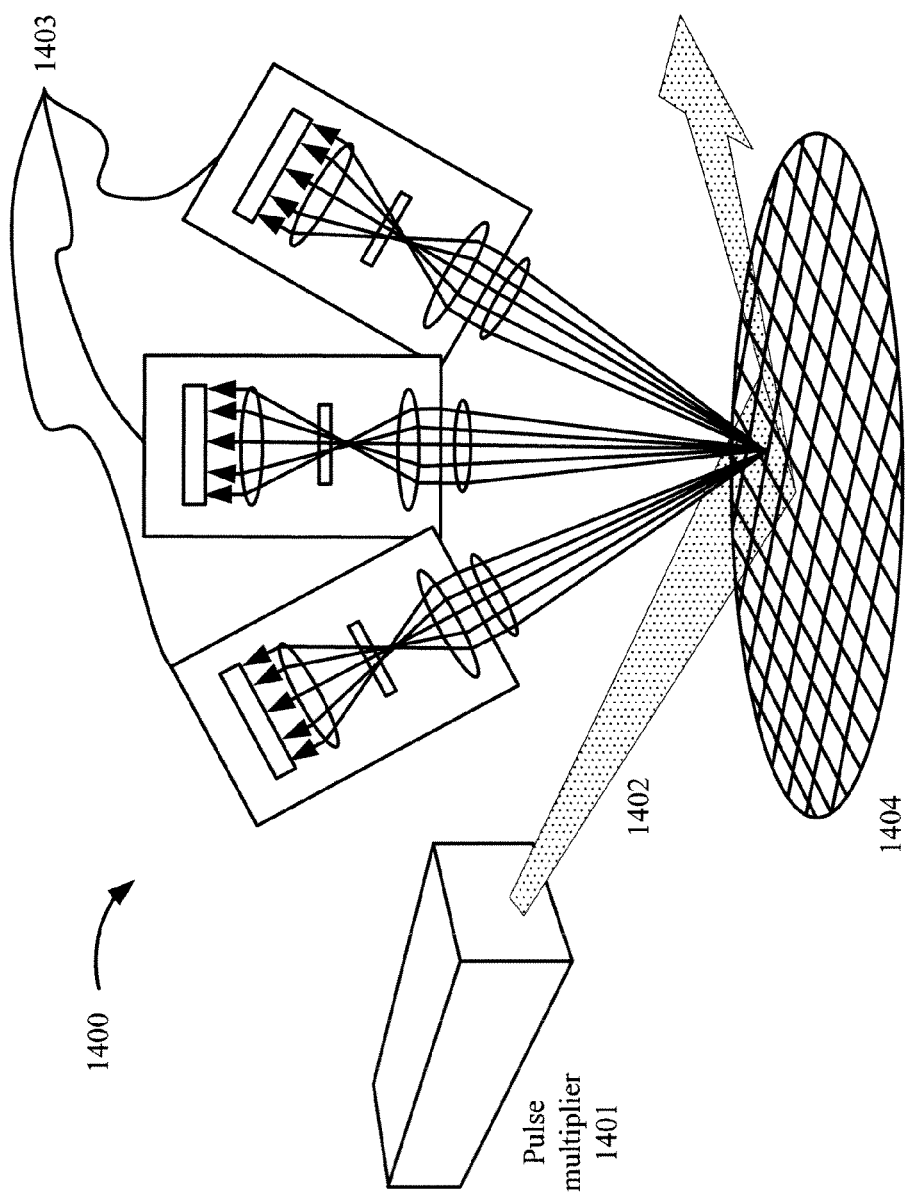
FIG. 14 illustrates an exemplary patterned wafer inspection system including a pulse multiplier.

FIG. 14 illustrates an exemplary patterned wafer inspection system 1400 including a pulse multiplier 1401, which can provide both near-normal and oblique illumination (only oblique illumination 1402 shown for clarity). Pulse multiplier 1401 can generates pulses from a UV, DUV, or VUV laser. Advantageously, pulse multiplier 1401 can increase the repetition rate of the laser used, while reducing its peak power. In system 1400, multi-channel collection 1403 can provide a large collection area, binning, and channel fusion with an increased signal to noise ratio (SNR). Illumination polarization, as generated by pulse multiplier 1401, can provide previous layer suppression and defect selectivity. The illumination channels, which facilitate multi-channel collection 1403, can illuminate one or more spots, one or more narrow lines, or a rectangular area on wafer 1404. Detection channels can include Fourier filtering (for pattern suppression), polarization selection, angle range, and/or numerical aperture (NA) control.

Advantageously, metrology systems can also include the above-described pulse multipliers. Exemplary metrology systems can include, but are not limited to, an ellipsometer (see, e.g. U.S. Pat. No. 6,734,968, incorporated by reference herein), an angle-resolved reflectometer (see, e.g. U.S. Pat. No. 4,999,014 or U.S. Pat. No. 7,667,841, both incorporated by reference herein) or a photo-acoustic measurement system (see, e.g. U.S. Pat. No. 4,710,030, incorporated by reference herein).

Note that any inspection or metrology system including a pulse multiplier can be used in combination with a pulse-shaping device. Exemplary pulse-shaping devices include but are not limited to those described in U.S. patent application Ser. No. 13/061,936 filed Mar. 2, 2011, which is a National Stage application of PCT Published Application WO2010/037106, which claims priority of U.S. Provisional Application 61/100,990, all applications being incorporated by reference herein. Such pulse-shaping devices can be used to reduce the coherence of each laser pulse or otherwise modify the shape of the pulse.

Figure 15:
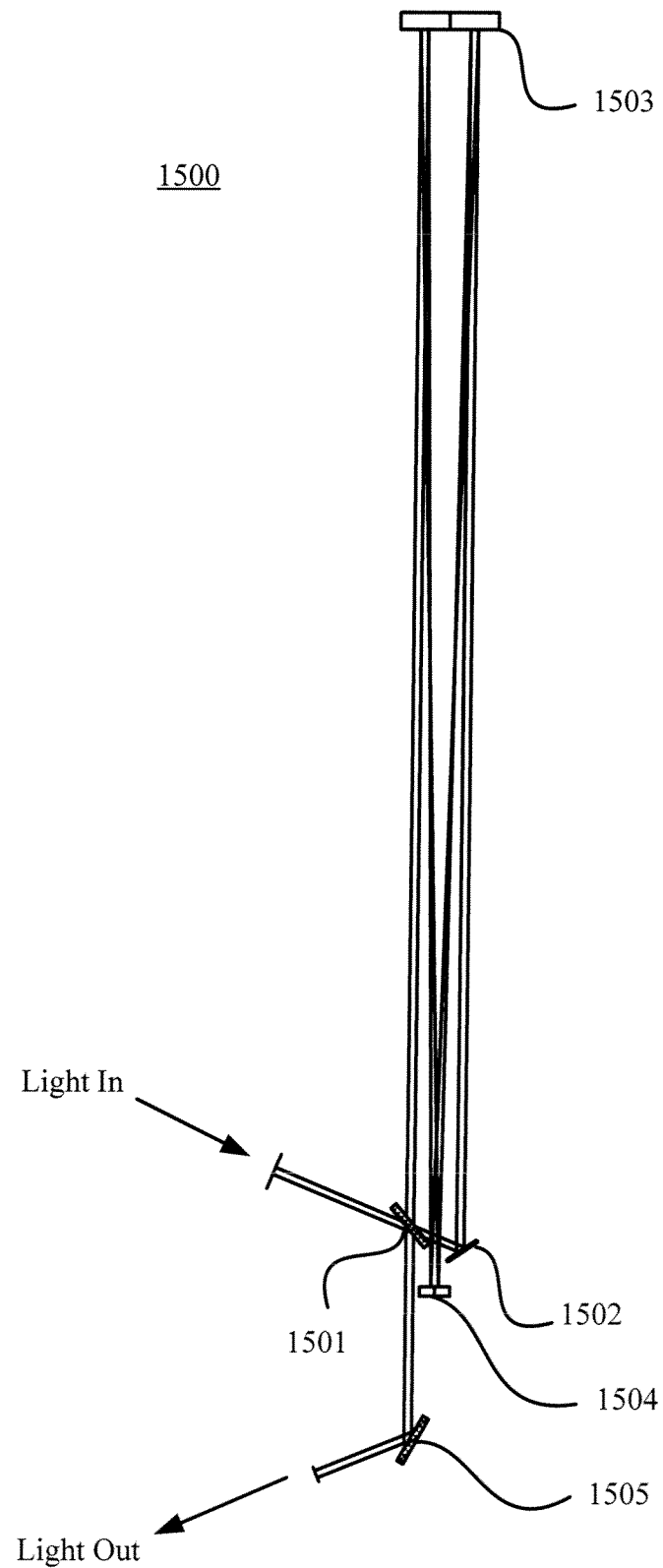
FIG. 15 illustrates another exemplary pulse multiplier.

FIG. 15 illustrates an exemplary pulse multiplier 1500 including mirrors and at least one half-wave plate In this embodiment, pulse multiplier 1500 can include a polarizing beam splitter 1501, which directs the incoming light to a flat mirror 1502. In one embodiment, a half-wave plate (not shown for simplicity) is positioned between polarizing beam splitter 1501 and mirror 1502. In other embodiments, one or more half-wave plates can be positioned as shown in other pulse multiplier embodiments described above.

Flat mirror 1502 reflects the light to a first spherical mirror 1503, which in turn directs the light to a second spherical mirror 1504. Second spherical mirror 1504 then directs the light back to first spherical mirror 1503, which in turn directs the light through polarizing beam splitter 1501. In one embodiment, first spherical mirror 1503 can have a 2× radius of second spherical mirror 1504. Note that first spherical mirror 1503 and second spherical mirror 1504 can be positioned to parallel positions, wherein the decenter of first spherical mirror 1503 can determine the relative position of second spherical mirror 1504. As shown in FIG. 15, polarizing beam splitter 1501 can have a Brewster angle, although in other embodiments, polarizing beam splitter 1501 can have a 45 degree angle. In one embodiment, the mirrors used in pulse multiplier 1500 can be mounted on a rail or in a tube for a compact and stable design. The practical convenience of this implementation is a notable feature. Note that geometric aberrations can be reduced to much lower than the diffraction limit by limiting the light beam diameter to, for example, less than a few mm extent, depending on laser beam quality requirements. In one embodiment, an optional polarizing beam splitter 1505 can be included at the output of pulse multiplier 1500 to improve polarization contrast.

Notably, the pulse multiplier can inexpensively reduce the peak power per pulse while increasing the number of pulses per second with minimal total power loss. The pulse multiplier can advantageously enable high speed inspection and metrology with off-the-shelf lasers. Dark-field inspection systems rely on laser light sources. The above-described pulse multiplier allows those systems to use lasers that would otherwise have too low a pulse repetition rate and provides a potential alternative to extremely high repetition rate UV lasers or CW lasers if no appropriate laser is available, or available lasers are too expensive or unreliable.

A detailed description of one or more embodiments of the invention is provided above along with accompanying figures that illustrate the principles of the invention. The invention is described in connection with such embodiments, but the invention is not limited to any embodiment.

For example, in one embodiment, the optical components can be coated with appropriate coatings for the laser wavelength. Each surface of the transmission elements, i.e. lens(es), and waveplate(s), can also have an anti-reflection coating that minimizes the amount of laser energy reflected at each surface. The mirrors can be polished and coated with a coatings designed to maximize the reflection and minimize scattering at the laser wavelength.

Figure 16:
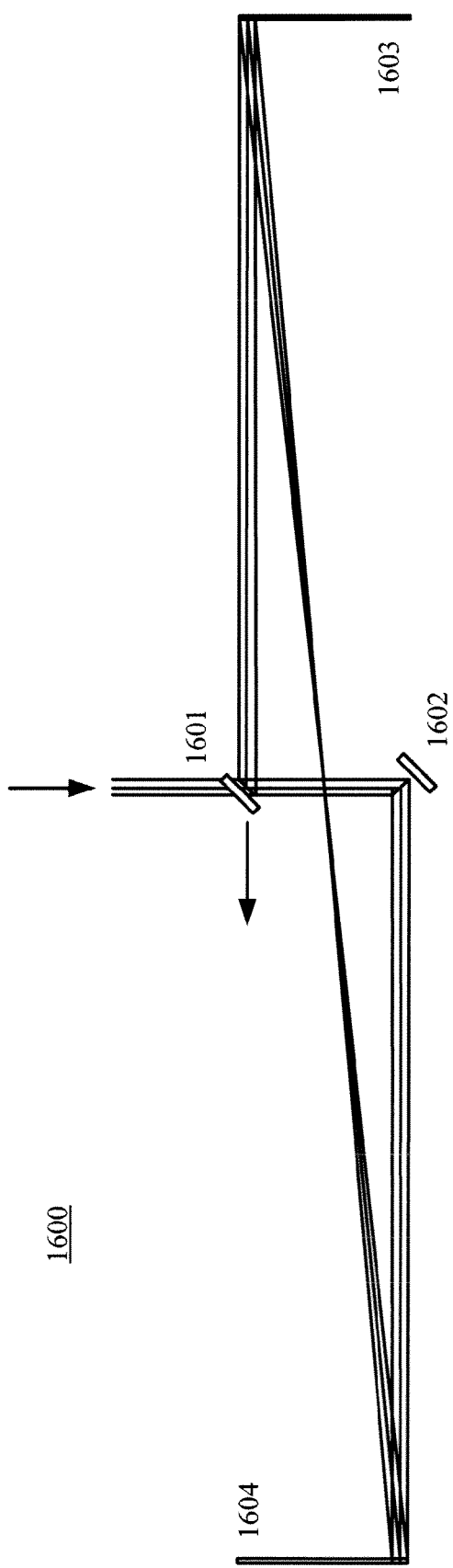
FIG. 16 illustrates a ring cavity that can be implemented using only reflective optics.

Note that a ring cavity can also be implemented using reflective optics as shown by ring cavity 1600, shown in FIG. 16. In this embodiment, the image relay can be facilitated by beamsplitter 1601, mirror 1602, spherical lens 1603, and spherical lens 1604. The principle is much the same as with the above-described lens systems, but with fewer interacting surfaces and potentially less loss.

Figure 17:
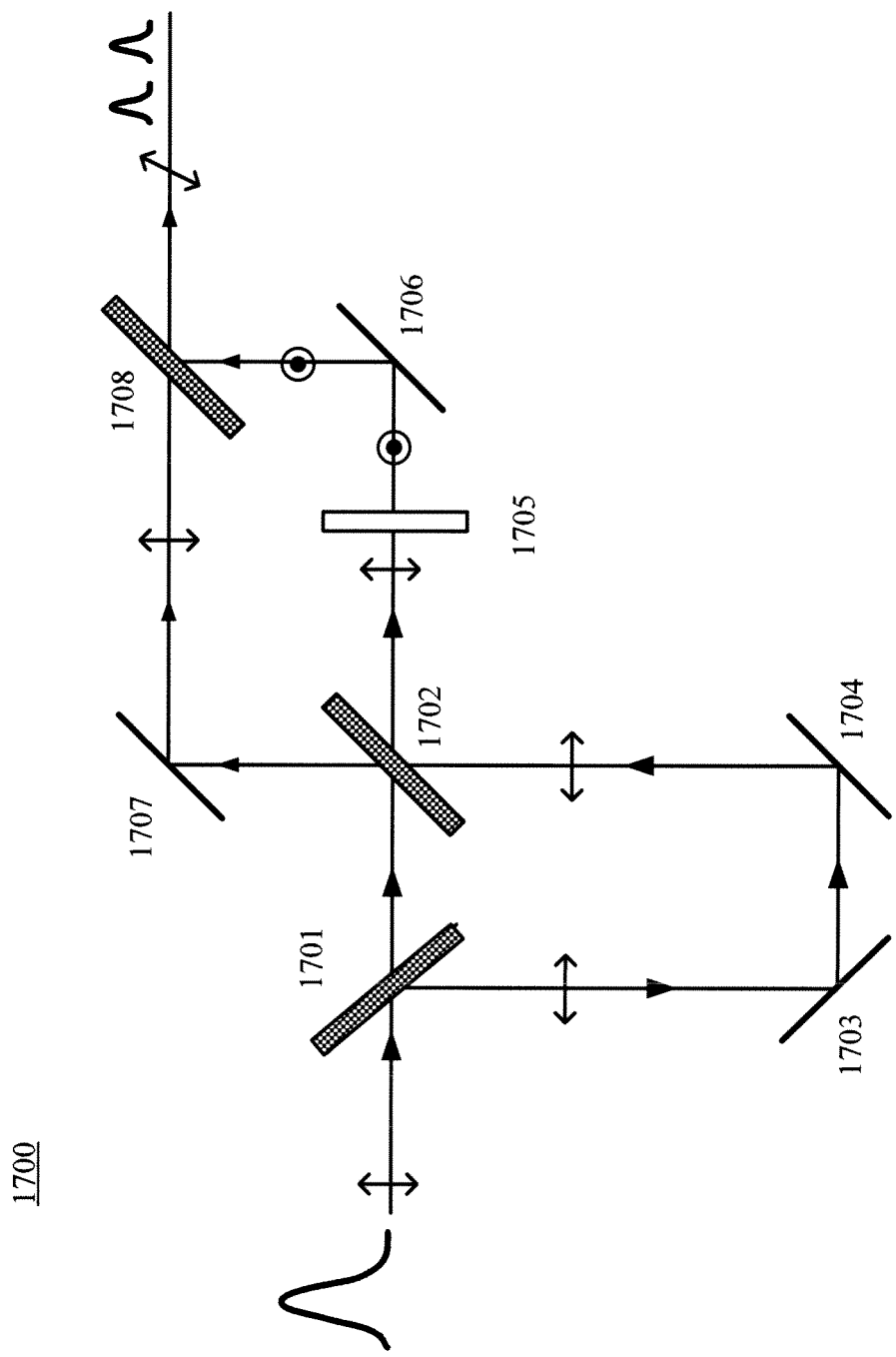
FIG. 17 illustrates another exemplary pulse multiplier.

FIG. 17 illustrates another exemplary pulse multiplier 1700 configured to generate pulse trains from each input pulse. An input pulse impinges on a non-polarizing beam splitter 1701, which transmits half of its light to a non-polarizing beam splitter 1702 and reflects the remaining half of its light to a mirror 1703. Mirror 1703 reflects that light to mirror 1704, which in turn reflects that light to non-polarizing beam splitter 1702. The total distance that the light reflected by beam splitter 1701 travels before arriving at beam splitter 1702 is chosen such that it introduces delay equals to the inverse of double the repetition rate of the incident light. In turn, non-polarizing beam splitter 1702 transmits half and reflects half of its light received from each of non-polarizing beam splitter 1701 and mirror 1704, therefore producing two beams with doubled pulse repetition rates. A half-wave plate 1705 and a mirror 1707 receive the light transmitted and reflected by non-polarizer beam splitter 1702. A mirror 1706 receives the two waves generated by half-wave plate 1705. A polarizing beam splitter 1708 receives the reflected light from both mirrors 1706 and 1707. Polarizing beam splitter 1708 combines the in-phase light and generates a forty-five degree angle output polarization for the pulse train (i.e. a repetition rate doubling scheme).

Figure 18:
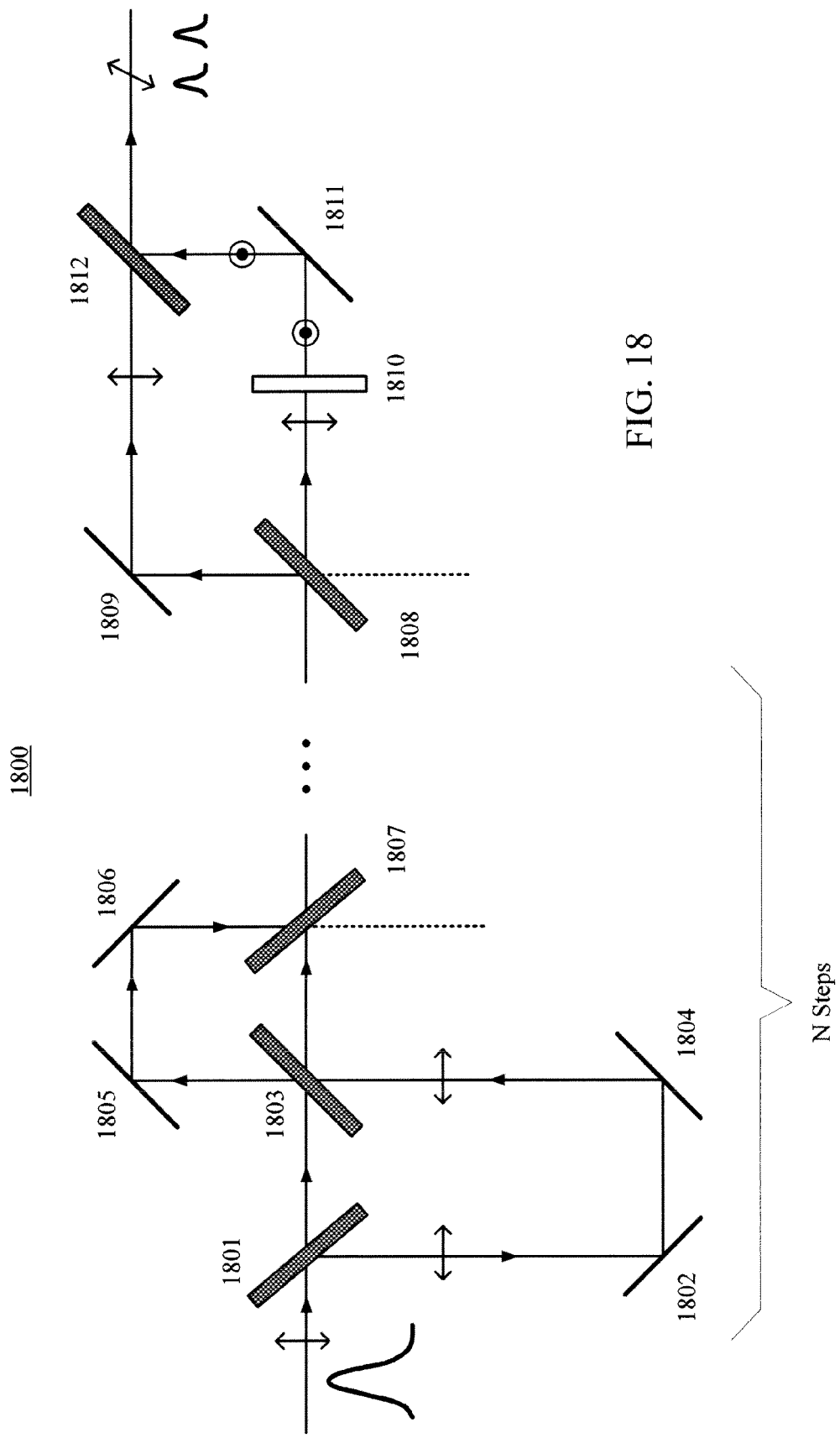
FIG. 18 illustrates another exemplary pulse multiplier.

FIG. 18 illustrates another exemplary pulse multiplier 1800 configured to generate pulse trains from each input pulse. An input pulse impinges on a non-polarizing beam splitter 1801, which transmits half of its light to a non-polarizing beam splitter 1803 and reflects the remaining half of its light to a mirror 1802. Mirror 1802 reflects that light to mirror 1803, which in turn reflects the light to non-polarizing beam splitter 1803. Non-polarizing beam splitter 1803 splits the received light between a mirror 1805 and a non-polarizing beam splitter 1807. Mirror 1805 reflects its light to a mirror 1806, which in turn reflects the light to non-polarizing beam splitter 1807. Notably, pulse multiplier 1800 includes N steps, wherein each step includes the above-described non-polarizing beam splitters and mirrors and results in 2× increase in pulse repetition rate to a total of $2^N\times$ after N steps. A non-polarizing beam splitter 1808 receives the transmitted light from the last step and splits the light between a mirror 1809 and a half-wave plate 1810. A mirror 1811 reflects the light output by half-wave plate 1810 to a polarizing beam splitter 1812, which also receives reflected light from mirror 1809. Polarizing beam splitter 1812 generates lights at a 45 degree output polarization.

The scope of the invention is limited only by the claims and the invention encompasses numerous alternatives, modifications and equivalents. Numerous specific details are set forth in the above description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The invention claimed is:

1. A pulse multiplier for converting input laser pulses transmitted at an input repetition pulse frequency into output pulsed light having an output repetition frequency that is greater than the input pulse frequency, the pulse multiplier comprising:
    a polarizing beam splitter positioned to receive each input laser pulse of the input laser pulses;
    a wave plate positioned to receive light from the polarized beam splitter and configured to generate a first set of pulses and a second set of pulses, the first set of pulses having a different polarization than the second set of pulses; and
    a set of mirrors configured to create a ring cavity including the polarizing beam splitter and the wave plate,
    wherein the polarizing beam splitter is configured to transmit all light of said each input laser pulse into the ring cavity, to transmit the first set of pulses such that the first set of pulses exit the ring cavity and form said output pulsed light, and to reflect the second set of pulses into the ring cavity, and
    wherein the ring cavity is configured such that the first set of pulses exiting the pulse multiplier have an output repetition pulse frequency that is at least double the input repetition pulse frequency.

2. The pulse multiplier of claim 1, wherein the wave plate includes a half-wave plate.

3. The pulse multiplier of claim 2, wherein the half-wave plate is set at 27.3678 degrees.

4. The pulse multiplier of claim 1, wherein the wave plate includes a quarter-wave plate.

5. The pulse multiplier of claim 1, further including a lens for uniformly shaping the pulses in the ring cavity.

6. The pulse multiplier of claim 1, further including a plurality of lenses for uniformly shaping the pulses in the ring cavity.

7. The pulse multiplier of claim 6, wherein the plurality of lenses is implemented with two image relay tubes.

8. The pulse multiplier of claim 6, wherein the plurality of lenses consists of two or four lenses.

9. The pulse multiplier of claim 1, wherein the mirror set includes a composite mirror.

10. The pulse multiplier of claim 1, wherein the mirror set creates two ring cavities that share the polarizing beam splitter and the wave plate.

11. A system comprising:
    a pulse multiplier for converting input laser pulses transmitted at an input repetition pulse frequency into output pulsed light having an output repetition frequency that is greater than the input pulse frequency, the pulse multiplier including:
    a polarizing beam splitter positioned to receive each input laser pulse of the input laser pulses;
    a wave plate positioned to receive light from the polarized beam splitter and configured to generate a first set of pulses and a second set of pulses, the first set of pulses having a different polarization than the second set of pulses; and
    a set of mirrors configured to create a ring cavity including the polarizing beam splitter and the wave plate,
    wherein the polarizing beam splitter is configured to transmit all light of said each input laser pulse into the ring cavity, to transmit the first set of pulses such that the first set of pulses exit the ring cavity and form said output pulsed light, and to reflect the second set of pulses into the ring cavity, and
    wherein the ring cavity is configured such that the first set of pulses exiting the pulse multiplier have an output repetition pulse frequency that is at least double the input repetition pulse frequency.

12. The system of claim 11, wherein the system implements one of an unpatterned wafer inspection system, a patterned wafer inspection system, a mask inspection system, or a metrology system.

* * * * *